(12) United States Patent
Bernareggi et al.

(10) Patent No.: US 8,426,625 B2
(45) Date of Patent: Apr. 23, 2013

(54) BIS-PLATINUM COMPLEXES WITH ANTITUMOR ACTIVITY

(75) Inventors: Alberto Bernareggi, Bresso (IT); Mario Grugni, Novate (IT); Giulio Mariotti, Milan (IT); Ernesto Menta, Cernusco Sul Naviglio (IT); Gianluca Pardi, Ripafratta (IT); Paolo Pavesi, Bresso (IT); Gabriella Pezzoni, Bresso (IT); Paolo Nicoli, Bresso (IT); Sergio De Munari, Milan (IT)

(73) Assignee: Cell Therapeutics, Inc., Seattle, WA (US)

( * ) Notice: Subject to any disclaimer, the term of this patent is extended or adjusted under 35 U.S.C. 154(b) by 635 days.

(21) Appl. No.: 12/086,547

(22) PCT Filed: Dec. 21, 2006

(86) PCT No.: PCT/EP2006/012366
§ 371 (c)(1),
(2), (4) Date: Jul. 29, 2010

(87) PCT Pub. No.: WO2007/071415
PCT Pub. Date: Jun. 28, 2007

(65) Prior Publication Data
US 2010/0292322 A1 Nov. 18, 2010

(30) Foreign Application Priority Data
Dec. 22, 2005 (IT) .............................. MI2005A2449

(51) Int. Cl.
*C07F 15/00* (2006.01)
*A61K 31/28* (2006.01)
(52) U.S. Cl.
USPC .......................................... 556/137; 514/492
(58) Field of Classification Search .................. 556/137; 514/492
See application file for complete search history.

(56) References Cited

U.S. PATENT DOCUMENTS

| | | | |
|---|---|---|---|
| 4,797,393 | A | 1/1989 | Farrell et al. |
| 4,871,528 | A | 10/1989 | Tognella et al. |
| 5,107,007 | A | 4/1992 | Farrell |
| 5,117,022 | A | 5/1992 | Khokhar et al. |
| 6,022,892 | A | 2/2000 | Farrell et al. |
| 6,596,889 | B1 | 7/2003 | Menta et al. |
| 6,613,799 | B1 | 9/2003 | Maeda et al. |

FOREIGN PATENT DOCUMENTS

| | | |
|---|---|---|
| EP | 1-968-991 B1 | 1/2012 |
| GB | 2-174-905 A | 11/1996 |
| WO | 91/03482 A1 | 3/1991 |
| WO | 98/03519 A2 | 1/1998 |
| WO | 03/018594 A1 | 6/2003 |
| WO | 2007/071415 A1 | 6/2007 |

OTHER PUBLICATIONS

ISR of PCT/EP2006/012366, mailed Apr. 24, 2007, 3 Pages.
Carter et al., "Cisplatin: current status and new developments," A.W. Prestayk et al. Academic Press, 125-47, 1980, 25 Pages.
Douple et al., "The use of platinum chemotherapy to potentiate radiotherapy," *Platinum Metals Rev.* 29(3):118-25, 1985.
Farrell et al., "Trypanocidal and antitumour activity of plantinum-metal and platinum-metal-drug dual-function complexes," *Biochemical Pharmacology* 33(7):961-71, 1984.
Freireich et al., "Quantitative comparison of toxicity of anticancer agents in mouse, rat, hamster, dog, monkey, and man," *Cancer Chemotherapy Reports* 50(4):219-44, May 1966.
Jacobs et al., "Plasma and cerebrospinal fluid pharmacokinetics of intravenous oxaliplatin, cisplatin, and carboplatin in nonhuman primates," *Clinical Cancer Research* 11:1669-74, Feb. 15, 2005.
Wong et al., "Current status of platinum-based antitumor drugs," *Chem. Rev.* 99(9):2451-66, 1999.

*Primary Examiner* — Porfirio Nazario Gonzalez
(74) *Attorney, Agent, or Firm* — Seed IP Law Group PLLC

(57) ABSTRACT

A compound of general formula (I): in which: R is selected from the group consisting of $(C_1-C_{25})$alkyl, $(C_2-C_{25})$alkenyl, aryl, $(C_7-C_{10})$aralkyl; n and m are each independently an integer of two to eight; p is one or two; A is selected from the group consisting of —B—, —B—$(CH_2)_r$—B—, —B—$(CH_2)_r$—B—$(CH_2)_z$—B—, wherein r and z are an integer from 2 to 8, B is a —NR$^1$— or —N(R$^2$)$_2$$^+$1/pQ$^{-p}$ group, in which R1 is selected from hydrogen, $(C_1-C_4)$alkyl, $(C_1-C_4)$ acyl, tert-butoxycarbonyl, and R$^2$ is selected from hydrogen and $(C_1-C_4)$alkyl; Q$^{-p}$ is an anion selected from chloride, bromide, iodide, nitrate, sulphate, hydrogen sulphate, perchlorate, R$^3$COO$^-$ wherein R$^3$ has the same meanings as R, independently from one another and R$^4$—O—SO$_3^-$ wherein R$^4$ is $(C_2-C_{14})$alkyl with the proviso that, when Q$^{-p}$ is selected from chloride, bromide, iodide, nitrate, sulphate, hydrogen sulphate, perchlorate, R is not $(C_1-C_4)$alkyl.

(I)

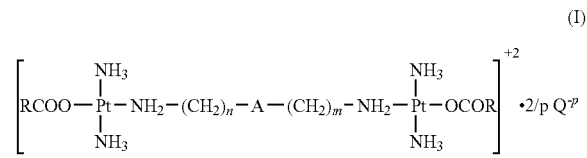

17 Claims, No Drawings

BIS-PLATINUM COMPLEXES WITH ANTITUMOR ACTIVITY

The present invention includes platinum complexes having antitumor activity, a method for the preparation thereof, pharmaceutical compositions containing them and uses thereof including the preparation of a medicament useful for the treatment of tumours.

Platinum complexes are amongst the most effective chemotherapeutics for the treatment of solid tumors. In particular, cisplatin [cis-dichlorodiaminoplatinum(II); CDDP] is one of the most widely used and effective antitumour agents, even though its administration is affected by severe side effects. Tumours that can be treated with this medicament comprise testicle, ovary, bladder and head/neck tumours. Since its introduction in therapy, cisplatin has been the drug of election for the curative therapy of germinal cells tumours and for the prolongation of survival therapy in ovary tumours. Successful treatment with cisplatin is limited mainly due to the fact that some tumour cells become drug-resistant. Moreover, the majority of solid tumors (for example lung, colon-rectum and stomach tumours) are not responsive to cisplatin or other chemotherapic agents (E. Wong, C. M. Giandomenico, Current Status of Platinum-Based Antitumor Drugs, Chem. Rev. 1999, 99, 2451-2466).

In order to identify platinum complexes with reduced toxicity, a wide antitumor activity spectrum and devoid of cross-resistance with cisplatin, a number of analogues have been studied over the last decades. These efforts have led to second-generation platinum complexes showing an antitumour activity profile similar to cisplatin in clinical studies. Among them, carboplatin, the second platinum complex to enter the market, has an antitumour activity spectum similar to cisplatin, while being devoid of its toxicity. A third-generation platinum complex recently introduced in clinic is oxaliplatinum. Other complexes under study are AMD0473 and satraplatinum. Nevertheless, it seems that none of these analogues overcomes the main problems of the therapy with cisplatin, i.e. none of them has widened the panel of treatment-responsive tumours, nor has it reduced the onset of tumour resistance.

Finally, another problem associated with platinum complexes currently used in therapy is that after intravenous administration, these complexes tend to irreversibly bind, by means of covalent bonds, to plasma proteins. The kinetics of this process depends on the contact time and more than 90% of the drug binds within few hours from administration. The high irreversible binding to plasma proteins can reduce the effectiveness of the compounds in humans (S. S. Jacobs et al., Clinical Cancer Research, Vol. 11, 1669-1674, 2005 and references cited).

Cisplatin-like liposoluble platinum complexes are disclosed in U.S. Pat. Nos. 5,117,022 and 6,613,799. The compounds disclosed in U.S. Pat. No. 5,117,022 can be incorporated in liposomes, whereas the complexes disclosed in U.S. Pat. No. 6,613,799 have high specificity and selectivity for the tumour cells when administered in a contrast medium such as lipiodol.

Bisplatinum complexes useful for the treatment of tumours characterized by the presence of a diamino or polyamino ligand that links the two platinum atoms together are disclosed in U.S. Pat. Nos. 4,797,393, 5,107,007, 6,022,892 and 6,596,889.

In particular, U.S. Pat. Nos. 6,022,892 and 6,596,889 disclose bisplatinum complexes characterized by the presence of a polyamino ligand. These compounds have a potent cytotoxic activity towards cisplatin-resistant murine and human tumour lines, such as the L1210/CDDP murine leukemia line and the A2780/CDDP human ovarian carcinoma line. The in vivo activity in a cisplatin-resistant experimental tumour is also reported for these compounds.

The applicant of the present application has found that, in the presence of human plasma, also the bisplatinum complexes disclosed in U.S. Pat. No. 6,022,892 irreversibly bind to plasma proteins, as explained above. Moreover, it has been found that the fraction of drug which is free in the plasma water and which is reversibly bound to proteins undergoes rapid and progressive degradation to give pharmacologically inactive species deriving from the removal of platinum from the polyamino ligand. These species are deemed to form as a consequence of chemical instability of the complexes in the plasma, probably due to their interaction with endogenous molecules that contain thiol nucleophiles such as, for example, cysteine or glutathione residues. The high binding level of the platinum compounds to human plasma proteins probably promotes this interaction. The rapid degradation in human plasma and the high irreversible binding to plasma proteins can impair the effectiveness of the compounds in humans. There is therefore the need for bisplatinum complexes which do not present these unfavourable properties.

As disclosed herein for the present invention, it has now surprisingly been found that bisplatinum complexes characterized by the presence of certain carboxylato ligands in the platinum coordination sphere bind plasma proteins less than the bisplatinum complexes cited above, show a better stability in the plasma towards deplatination and are able to inhibit tumour growth in various experimental models.

The compounds of the invention have the following general formula (I):

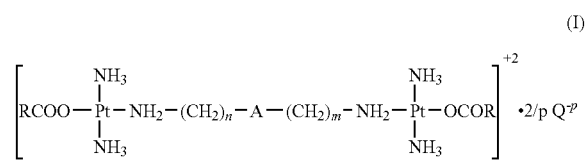

in which:

R is selected from the group consisting of $(C_1\text{-}C_{25})$alkyl, $(C_2\text{-}C_{25})$alkenyl, aryl, $(C_7\text{-}C_{10})$aralkyl;

n and m are each independently an integer of two to eight;

p is one or two;

A is selected from the group consisting of —B—, —B—$(CH_2)_r$—B—, —B—$(CH_2)_r$—B—$(CH_2)_z$—B—, wherein r and z are integers from 2 to 8, B is a —NR$^1$— or a —N(R$^2$)$_2^+$ 1/pQ$^{-p}$ group, in which R$^1$ is selected from hydrogen, $(C_1\text{-}C_4)$alkyl, $(C_1\text{-}C_4)$acyl, tert-butoxycarbonyl and R$^2$ is selected from hydrogen and $(C_1\text{-}C_4)$alkyl;

Q$^{-p}$ is an anion selected from chloride, bromide, iodide, nitrate, sulphate, hydrogen sulphate, perchlorate, R$^3$COO$^-$ wherein R$^3$ has the same meanings as R, independently from one another, and R$^4$—O—SO$_3^-$ wherein R$^4$ is $(C_2\text{-}C_{14})$alkyl with the proviso that, when Q$^{-p}$ is selected from chloride, bromide, iodide, nitrate, sulphate, hydrogen sulphate, perchlorate, R is not $(C_1\text{-}C_4)$alkyl.

The invention also comprises the enantiomers and the diastereomers of the compounds of formula (I).

The term $(C_1\text{-}C_{25})$alkyl means a straight or branched alkyl residue from 1 to 25 carbon atoms, optionally substituted with from one to five hydroxy groups, $(C_1\text{-}C_4)$alkoxy, $(C_1\text{-}C_4)$acyloxy, $(C_1\text{-}C_4)$alkoxycarbonyl, halogen, $(C_1\text{-}C_4)$aminocarbonyl —CONR$_a$R$_b$, wherein R$_a$ and R$_b$ are independently H, ($C_1$-$C_4$)alkyl and aryl, ($C_1$-$C_4$) alkylcarbonylamino, —$NR_aCOR_b$, —$OCONR_aR_b$ wherein $R_a$ and $R_b$ are as defined above, —$NR_aCOOR_c$ wherein $R_a$ is as defined above and $R_c$ is $C_1$-$C_4$ alkyl, aryl; said alkyl chain being optionally interrupted by 1 to 12 oxygen atoms, with the proviso that when the number of said oxygen atoms is higher than 2, they are separated by at least 2 carbon atoms.

The term ($C_2$-$C_{25}$)alkenyl means a straight or branched alkenyl residue consisting of 2 to 25 carbon atoms and containing from 1 to 8 double bonds, each double bond being independently in the cis or trans configuration and the residue being an optionally substituted alkenyl with one to five hydroxy groups, ($C_1$-$C_4$)alkoxy, ($C_1$-$C_4$)acyloxy, ($C_1$-$C_4$) alkoxycarbonyl, halogen, —$CONR_aR_b$, wherein $R_a$ and $R_b$ are independently H, ($C_1$-$C_4$)alkyl and aryl, —$NR_aCOR_b$, —$OCONR_aR_b$ wherein $R_a$ and $R_b$ are as defined above, —$NR_aCOOR_c$ wherein $R_a$ is as defined above and $R_c$ is ($C_1$-$C_4$)alkyl, aryl; with the proviso that said hydroxy, alkoxy, acyloxy, alkylcarbonylamino, alkylaminocarbonyloxy and alkoxycarbonylamino groups cannot be linked to the carbon atoms forming carbon-carbon double bonds.

Aryl preferably means a phenyl, diphenyl or naphthyl group unsubstituted or substituted with one to three substituents selected from halogen atoms, nitro groups, cyano, hydroxy, ($C_1$-$C_4$)alkoxy, ($C_1$-$C_4$)acyloxy, ($C_1$-$C_3$)haloalkoxy, ($C_1$-$C_4$)alkoxycarbonyl, carboxy, ($C_2$-$C_4$)acyl. Aryl is preferably an unsubstituted phenyl group or a phenyl group substituted as indicated above.

Preferably, the R group taken together with the carboxylate group to which it is bound is the residue of a saturated, mono-unsaturated or poly-unsaturated fatty acid. Preferred examples are: saturated fatty acids having 10 to 24 carbon atoms such as, for example, capric acid (decanoic acid), neodecanoic acid, lauric acid (dodecanoic acid), myristic acid (tetradecanoic acid), palmitic acid (hexadecanoic acid), stearic acid (octadecanoic acid), arachidic acid (eicosanoic acid), behenic acid (docosanoic acid), lignoceric acid (tetracosanoic acid), 15-hydroxypentadecanoic acid, 16-hydroxypalmitic acid (16-hydroxyhexadecanoic acid; juniperic acid), 6-hydroxypalmitic acid, (R)-7-hydroxyhexadecanoic acid, 17-hydroxyheptadecanoic acid, (S)-9-hydroxyoctadecanoic acid, (S)-13-hydroxyoctadecanoic acid, 12-hydroxystearic acid (12-hydroxyoctadecanoic acid), erythro-6,7-dihydroxyoctadecanoic acid, threo-9,10-dihydroxystearic acid, erythro-9,10-dihydroxystearic acid, erythro-12,13-dihydroxyoctadecanoic acid, erythro-15,16-dihydroxyoctadecanoic acid; mono-unsaturated fatty acids having from 16 to 22 carbon atoms such as oleic acid (cis-9-octadecenoic acid), ricinoleic acid ((R)-12-hydroxy-cis-9-octadecenoic acid; 12-hydroxyoleic acid), erucic acid (cis-13-docosenoic acid); poly-unsaturated fatty acids such as linoleic acid (cis,cis-6,9-octadecadienoic acid), linoledaidic acid (trans, trans-9,12-octadecadienoic acid), linolenic acid (cis,cis,cis-9,12,15-octadecatrienoic acid), γ-linolenic acid (cis,cis,cis-6,9,12-octadecatrienoic acid), linolenelaidic acid (trans,trans,trans-9,12,15 octadecatrienoic acid), arachidonic acid (cis,cis,cis, cis-5,8,11,14-eicosatetraenoic acid), cis,cis,cis,cis,cis-5,8, 11,14,17-eicosapentaenoic acid (EPA), cis,cis,cis,cis,cis-4,7,10,13,16,19-docosahexenoic acid (DHA), 4(E),7(Z),10 (Z),13(Z),16(Z),19(Z)-docosahexaenoic acid.

Preferred $R^4$—O—$SO_3^-$ groups are n-hexyl sulphate, 2-ethylhexylsulphate, n-octylsulphate, n-decylsulphate, n-dodecylsulphate; particularly preferred is dodecylsulphate.

Particularly preferred compounds are those in which the $H_2N$—$(CH_2)_n$-A-$(CH_2)_m$—$NH_2$ moiety is one of the following residues:

$H_2N$—$(CH_2)_3$—$NH_2$+—$(CH_2)_4$—$NH_2$
$H_2N$—$(CH_2)_3$—$NH_2$+—$(CH_2)_4$—$NH_2$+—$(CH_2)_3$—$NH_2$
$H_2N$—$(CH_2)_6$—$NH_2$+—$(CH_2)_2$—$NH_2$+—$(CH_2)_6$—$NH_2$
$H_2N$—$(CH_2)_5$—$NH_2$+—$(CH_2)_4$—$NH_2$+—$(CH_2)_5$—$NH_2$.

In the present description, the expression "the residue of" means a radical, i.e. an uncompleted covalent bond form.

Examples of compounds of the invention are:

{μ-(1,8,11,18-tetraazaoctadecane-$N^1$,$N^{18}$)bis[trans-diamino(hexanoato-O)platinum(II)]}tetranitrate {μ-(1,8,11,18-tetraazaoctadecane-$N^1$,$N^{18}$)bis[trans-diamino(octanoato-O)platinum(II)]}tetranitrate {μ-(1,8,11,18-tetraazaoctadecane-$N^1$,$N^{18}$)bis[trans-diamino(decanoato-O)platinum(II)]}tetradecanoate {μ-(1,8,11,18-tetraazaoctadecane-$N^1$,$N^{18}$)bis[trans-diamino(undecanoato-O)platinum(II)]}tetraundecanoate {μ-(1,8,11,18-tetraazaoctadecane-$N^1$,$N^{18}$)bis[trans-diamino(dodecanoato-O)platinum(II)]}tetradodecanoate {μ-(1,8,11,18-tetraazaoctadecane-$N^1$,$N^{18}$)bis[trans-diamino(tridecanoato-O)platinum(II)]}tetratridecanoate {μ-(1,8,11,18-tetraazaoctadecane-$N^1$,$N^{18}$)bis[trans-diamino(myristato-O)platinum(II)]}tetramyristate {μ-(1,8,11,18-tetraazaoctadecane-$N^1$,$N^{18}$)bis[trans-diamino(palmitato-O)platinum(II)]}tetrapalmitate {μ-(1,8,11,18-tetraazaoctadecane-$N^1$,$N^{18}$)bis[trans-diamino(stearato-O)platinum(II)]}tetrastearate {μ-(1,8,11,18-tetraazaoctadecane-$N^1$,$N^{18}$)bis[trans-diamino(oleato-O)platinum(II)]}tetraoleate {μ-(1,8,11,18-tetraazaoctadecane-$N^1$,$N^{18}$)bis[trans-diamino(linoleato-O)platinum(II)]}tetralinoleate {μ-(1,8,11,18-tetraazaoctadecane-$N^1$,$N^{18}$)bis[trans-diamino(linolenato-O)platinum(II)]}tetralinolenate {μ-(1,8,11,18-tetraazaoctadecane-$N^1$,$N^{18}$)bis[trans-diamino(cis-4,7,10,13,16,19-docosahexenoato-O)platinum(II)]}tetra(cis-4,7,10,13,16,19-docosahexenoate)

{μ-(1,8,11,18-tetraazaoctadecane-$N^1$,$N^{18}$)bis[trans-diamino(cis-5, 8, 11, 14, 17-eicosapentenoato-O)platinum(II)]}tetra(cis-5,8,11,14,17-eicosapentaenoate)

{μ-(1,8,11,18-tetraazaoctadecane-$N^1$,$N^{18}$)bis[trans-diamino(ricinoleato-O)platinum(II)]}tetraricinoleate {μ-(1,8,11,18-tetraazaoctadecane-$N^1$,$N^{18}$)bis [trans-diamino(16-hydroxyhexadecanoato-O)platinum(II)]}tetra(16-hydroxyhexadecanoate)

{μ-(1,8,11,18-tetraazaoctadecane-$N^1$,$N^{18}$)bis[trans-diamino(12(R,S)-hydroxyoctadecanoato-O)platinum(II)]}tetra(12(R,S)-hydroxyoctadecanoate)

{μ-(1,7,12,18-tetraazaoctadecane-$N^1$,$N^{18}$)bis[trans-diamino(hexanoato-O)platinum(II)]}tetranitrate {μ-(1,7,12,18-tetraazaoctadecane-$N^1$,$N^{18}$)bis[trans-diamino(octanoato-O)platinum(II)]}tetranitrate {μ-(1,7,12,18-tetraazaoctadecane-$N^1$,$N^{18}$)bis[trans-diamino(decanoato-O)platinum(II)]}tetradecanoate {μ-(1,7,12,18-tetraazaoctadecane-$N^1$,$N^{18}$)bis[trans-diamino(undecanoato-O)platinum(II)]}tetraundecanoate {μ-(1,7,12,18-tetraazaoctadecane-$N^1$,$N^{18}$)bis[trans-diamino(dodecanoato-O)platinum(II)]}tetradodecanoate {μ-(1,7,12,18-tetraazaoctadecane-$N^1$,$N^{18}$)bis[trans-diamino(tridecanoato-O)platinum(II)]}tetratridecanoate {μ-(1,7,12,18-tetraazaoctadecane-$N^1$,$N^{18}$)bis[trans-diamino(myristato-O)platinum(II)]}tetramyristate {μ-(1,7,12,18-tetraazaoctadecane-$N^1$,$N^{18}$)bis[trans-diamino(palmitato-O)platinum(II)]}tetrapalmitate {μ-(1,7,12,18-tetraazaoctadecane-$N^1$,$N^{18}$)bis[trans-diamino(stearato-O)platinum(II)]}tetrastearate {μ-(1,7,12,18-tetraazaoctadecane-$N^1$,$N^{18}$)bis[trans-diamino(oleato-O)platinum(II)]}tetraoleate {μ-(1,7,12,18-tetraazaoctadecane-N$^1$,N$^{18}$)bis[trans-diamino(linoleato-O)platinum(II)]}tetralinoleate {μ-(1,7,12,18-tetraazaoctadecane-N$^1$,N$^{18}$)bis[trans-diamino(linolenato-O)platinum(II)]}tetralinolenate {μ-(1,7,12,18-tetraazaoctadecane-N$^1$,N$^{18}$)bis[trans-diamino(cis-4,7,10,13,16,19-docosahexenoato-O)platinum(II)]}tetra(cis-4,7,10,13,16,19-docosahexenoate)

{μ-(1,7,12,18-tetraazaoctadecane-N$^1$,N$^{18}$)bis[trans-diamino(cis-5, 8, 11, 14,17-eicosapentenoato-O)platinum(II)]}tetra(cis-5,8,11,14,17-eicosapentaenoate)

{μ-(1,7,12,18-tetraazaoctadecane-N$^1$,N$^{18}$)bis[trans-diamino(ricinoleato-O)platinum(II)]}tetraricinoleate {μ-(1,7,12,18-tetraazaoctadecane-N$^1$,N$^{18}$)bis[trans-diamino(16-hydroxyhexadecanoato-O)platinum(II)]}tetra(16-hydroxyhexadecanoate)

{μ-(1,7,12,18-tetraazaoctadecane-N$^1$,N$^{18}$)bis[trans-diamino(12(R,S)-hydroxyoctadecanoato-O)platinum(II)]}tetra(12(R,S)-hydroxyoctadecanoate)

{μ-(1,5,10,14-tetraazatetradecane-N$^1$N$^{14}$)bis[trans-diamino(hexanoato-O)platinum(II)]}tetranitrate {μ-(1,5,10,14-tetraazatetradecane-N$^1$,N$^{14}$)bis[trans-diamino(octanoato-O)platinum(II)]}tetranitrate {μ-(1,5,10,14-tetraazatetradecane-N$^1$,N$^{14}$)bis[trans-diamino(decanoato-O)platinum(II)]}tetradecanoate {μ-(1,5,10,14-tetraazatetradecane-N$^1$,N$^{14}$)bis[trans-diamino(undecanoato-O)platinum(II)]}tetraundecanoate {μ-(1,5,10,14-tetraazatetradecane-N$^1$,N$^{14}$)bis[trans-diamino(dodecanoato-O)platinum(II)]}tetradodecanoate {μ-(1,5,10,14-tetraazatetradecane-N$^1$,N$^{14}$)bis[trans-diamino(tridecanoato-O)platinum(II)]}tetratridecanoate {μ-(1,5,10,14-tetraazatetradecane-N$^1$,N$^{14}$)bis[trans-diamino(myristato-O)platinum(II)]}tetramyristate {μ-(1,5,10,14-tetraazatetradecane-N$^1$,N$^{14}$)bis[trans-diamino(palmitato-O)platinum(II)]}tetrapalmitate {μ-(1,5,10,14-tetraazatetradecane-N$^1$,N$^{14}$)bis[trans-diamino(stearato-O)platinum(II)]}tetrastearate {μ-(1,5,10,14-tetraazatetradecane-N$^1$,N$^{14}$)bis[trans-diamino(oleato-O)platinum(II)]}tetraoleate {μ-(1,5,10,14-tetraazatetradecane-N$^1$,N$^{14}$)bis[trans-diamino(linoleato-O)platinum(II)]}tetralinoleate {μ-(1,5,10,14-tetraazatetradecane-N$^1$,N$^{14}$)bis[trans-diamino(linolenato-O)platinum(II)]}tetralinolenate {μ-(1,5,10,14-tetraazatetradecane-N$^1$,N$^{14}$)bis[trans-diamino(cis-4,7,10,13,16,19-docosahexenoato-O)platinum(II)]}tetra(cis-4,7,10,13,16,19-docosahexenoate)

{μ-(1,5,10,14-tetraazatetradecane-N$^1$,N$^{14}$)bis[trans-diamino(cis-5,8,11,14,17-eicosapentenoato-O)platinum(II)]}tetra(cis-5,8,11,14,17-eicosapentaenoate)

{μ-(1,5,10,14-tetraazatetradecane-N$^1$,N$^{14}$)bis[trans-diamino(ricinoleato-O)platinum(II)]}tetraricinoleate {μ-(1,5,10,14-tetraazatetradecane-N$^1$,N$^{14}$)bis[trans-diamino(16-hydroxyhexadecanoato-O)platinum(II)]}tetra(16-hydroxyhexadecanoate)

{μ-(1,5,10,14-tetraazatetradecane-N$^1$,N$^{14}$)bis[trans-diamino(12(R,S)-hydroxyoctadecanoato-O)platinum(II)]}tetra(12(R,S)-hydroxyoctadecanoate)

{μ-(1,5,10-triazadecane-N$^1$,N$^{10}$)bis[trans-diamino(hexanoato-O)platinum(II)]}tetranitrate {μ-(1,5,10-triazadecane-N$^1$,N$^{10}$)bis[trans-diamino(octanoato-O)platinum(II)]}tetranitrate {μ-(1,5,10-triazadecane-N$^1$,N$^{10}$)bis[trans-diamino(decanoato-O)platinum(II)]}tetradecanoate {μ-(1,5,10-triazadecane-N$^1$,N$^{10}$)bis[trans-diamino(undecanoato-O)platinum(II)]}tetraundecanoate {μ-(1,5,10-triazadecane-N$^1$,N$^{10}$)bis[trans-diamino(dodecanoato-O)platinum(II)]}tetradodecanoate {μ-(1,5,10-triazadecane-N$^1$,N$^{10}$)bis[trans-diamino(tridecanoato-O)platinum(II)]}tetratridecanoate {μ-(1,5,10-triazadecane-N$^1$,N$^{10}$)bis[trans-diamino(myristato-O)platinum(II)]}tetramyristate {μ-(1,5,10-triazadecane-N$^1$,N$^{10}$)bis[trans-diamino(palmitato-O)platinum(II)]}tetrapalmitate {μ-(1,5,10-triazadecane-N$^1$,N$^{10}$)bis[trans-diamino(stearato-O)platinum(II)]}tetrastearate {μ-(1,5,10-triazadecane-N$^1$,N$^{10}$)bis[trans-diamino(oleato-O)platinum(II)]}tetraoleate {μ-(1,5,10-triazadecane-N$^1$,N$^{10}$)bis[trans-diamino(linoleato-O)platinum(II)]}tetralinoleate {μ-(1,5,10-triazadecane-N$^1$,N$^{10}$)bis[trans-diamino(linolenato-O)platinum(II)]}tetralinolenate {μ-(1,5,10-triazadecane-N$^1$,N$^{10}$)bis[trans-diamino(cis-4,7,10,13,16,19-docosahexenoato-O)platinum(II)]}tetra(cis-4,7,10,13,16,19-docosahexenoate)

{μ-(1,5,10-triazadecane-N$^1$,N$^{10}$)bis[trans-diamino(cis-5,8,11,14,17-eicosapentenoato-O)platinum(II)]}tetra(cis-5,8,11,14,17-eicosapentaenoate)

{μ-(1,5,10-triazadecane-N$^1$,N$^{10}$)bis[trans-diamino(ricinoleato-O)platinum(II)]}tetraricinoleate {μ-(1,5,10-triazadecane-N$^1$,N$^{10}$)bis[trans-diamino(16-hydroxyhexadecanoato-O)platinum(II)]}tetra(16-hydroxyhexadecanoate)

{μ-(1,5,10-triazadecane-N$^1$,N$^{10}$)bis[trans-diamino(12(R,S)-hydroxyoctadecanoato-O)platinum(II)]}tetra(12(R,S)-hydroxyoctadecanoate)

{μ-(1,8,11,18-Tetraazaoctadecane-N$^1$,N$^{18}$)bis[trans-diamino(16-hydroxypalmitato-O)platinum(II)]}tetra(16-hydroxypalmitate)

{μ-(1,7,12,18-Tetraazaoctadecane-N$^1$,N$^{18}$)bis[trans-diamino(16-hydroxypalmitato-O)platinum(II)]}tetra(16-hydroxypalmitate)

{μ-(1,5,10,14-Tetraazatetradecane-N$^1$,N$^{14}$)bis[trans-diamino(16-hydroxypalmitato-O)platinum(II)]}tetra(16-hydroxypalmitate)

{μ-(1,5,10-Triazadecane-N$^1$,N$^{10}$)bis[trans-diamino(16-hydroxypalmitato-O)platinum(II)]}tetra(16-hydroxypalmitate)

{μ-(1,7,12,18-Tetraazaoctadecane-N$^1$,N$^{18}$)bis[trans-diamino(butyrato-O)platinum(II)]}tetrabutyrate {μ-(1,7,12,18-Tetraazaoctadecane-N$^1$,N$^{18}$)bis[trans-diamino(butyrato-O)platinum(II)]}tetrabutyrate {μ-(1,5,10,14-Tetraazatetradecane-N$^1$,N$^{14}$)bis[trans-diamino(butyrato-O)platinum(II)]}tetrabutyrate {μ-(1,5,10-Triazadecane-N$^1$,N$^{10}$)bis[trans-diamino(butyrato-O)platinum(II)]}tetrabutyrate {μ-(1,8,11,18-Tetraazaoctadecane-N$^1$,N$^{18}$)bis[trans-diamino(caprylato-O)platinum(II)]}tetracaprylate {μ-(1,7,12,18-Tetraazaoctadecane-N$^1$,N$^{18}$)bis[trans-diamino(caprylato-O)platinum(II)]}tetracaprylate {μ-(1,5,10,14-Tetraazatetradecane-N$^1$,N$^{14}$)bis[trans-diamino(caprylato-O)platinum(II)]}tetracaprylate)

{μ-(1,5,10-Triazadecane-N$^1$,N$^{10}$)bis[trans-diamino(caprylato-O)platinum(II)]}tetracaprylate {μ-(1,8,11,18-Tetraazaoctadecane-N$^1$,N$^{18}$)bis[trans-diamino(caproato-O)platinum(II)]}tetracaprate {μ-(1,7,12,18-Tetraazaoctadecane-N$^1$,N$^{18}$)bis[trans-diamino(caproato-O)platinum(II)]}tetracaprate {μ-(1,5,10,14-Tetraazatetradecane-N$^1$,N$^{14}$)bis[trans-diamino(caproato-O)platinum(II)]}tetracaprate)

{μ-(1,5,10-Triazadecane-N$^1$,N$^{10}$)bis[trans-diamino(caproato-O)platinum(II)]}tetracaprate {μ-(1,8,11,18-Tetraazaoctadecane-N$^1$,N$^{18}$)bis[trans-diamino(pivalato-O)platinum(II)]}tetra(dodecylsulphate)

{μ-(1,7,12,18-Tetraazaoctadecane-$N^1,N^{18}$)bis[trans-diamino(pivalato-O)platinum(II)]}tetra(dodecylsulphate)

{μ-(1,5,10,14-Tetraazatetradecane-$N^1,N^{14}$)bis[trans-diamino(pivalato-O)platinum(II)]}tetra(dodecylsulphate)

{μ-(1,5,10-Triazadecane-$N^1,N^{10}$)bis[trans-diamino(pivalato-O)platinum(II)]}tetra(dodecylsulphate)

{μ-(1,8,11,18-Tetraazaoctadecane-$N^1,N^{18}$)bis[trans-diamino(capronato-O)platinum(II)]}tetra(dodecylsulphate)

{μ-(1,7,12,18-Tetraazaoctadecane-$N^1,N^{18}$)bis[trans-diamino(capronato-O)platinum(II)]}tetra(dodecylsulphate)

{μ-(1,5,10,14-Tetraazatetradecane-$N^1,N^{14}$)bis[trans-diamino(capronato-O)platinum(II)]}tetra(dodecylsulphate)

{μ-(1,5,10-Triazadecane-$N^1,N^{10}$)bis[trans-diamino(capronato-O)platinum(II)]}tetra(dodecylsulphate)

{μ-(1,8,11,18-Tetraazaoctadecane-$N^1,N^{18}$)bis[trans-diamino(butyrato-O)platinum(II)]}tetra(dodecylsulphate)

{μ-(1,7,12,18-Tetraazaoctadecane-$N^1,N^{18}$)bis[trans-diamino(butyrato-O)platinum(II)]}tetra(dodecylsulphate)

{μ-(1,5,10,14-Tetraazatetradecane-$N^1,N^{14}$)bis[trans-diamino(butyrato-O)platinum(II)]}tetra(dodecylsulphate)

{μ-(1,5,10-Triazadecane-$N^1,N^{10}$)bis[trans-diamino(butyrato-O)platinum(II)]}tetra(dodecylsulphate)

The compounds of formula (I) can be prepared by reaction of a compound of formula (II)

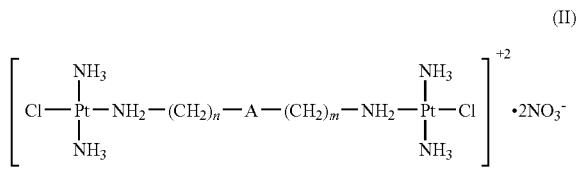

(II)

in which A has the same meanings as the compounds of formula (I), wherein p is 1 and $Q^{-p}$ is the nitrate anion, with at least two equivalents of silver nitrate, to give an intermediate which is subsequently reacted with at least two equivalents of a compound of formula (III)

RCOOM (III)

in which R has the same meanings as in formula (I) and M is the cation of an alkali, alkaline-earth metal or of a quaternary ammonium salt (for example, tetramethylammonium, tetrabutylammonium), to give a compound of formula (I) in which $Q^{-p}$ is the nitrate ($NO_3^-$) or carboxylate ($RCOO^-$) anion, wherein p is 1 and R is as defined in formula (I).

The reaction of the compounds of formula (II) with silver nitrate and the subsequent reaction with the compounds of formula (III) is generally carried out in a solvent such as water, dimethylformamide or mixtures thereof, operating at a temperature ranging from 10 to 60° C. and for a time ranging from 15 hours to 3 weeks. Preferably, 2 equivalents of a compound of formula III are used for each equivalent of the compound of formula II and the reaction is generally completed in 2 days.

The compounds of formula (I) in which $Q^{-p}$ is the nitrate anion can be obtained by reaction of a compound of formula II with at least two equivalents of silver carboxylate of formula (III')

RCOOAg (III')

The reaction is generally carried out in a solvent such as water, dimethylformamide or mixtures thereof, operating at a temperature ranging from 10 to 60° C. and for a time ranging from 15 hours to 3 weeks. Preferably a molar excess (2 equivalents) of the compound of formula III' is used and the reaction is generally completed in 2 days.

The compounds of formula (I) in which $Q^{-p}$ is $RCOO^-$ can be obtained by reaction of a compound of formula (II')

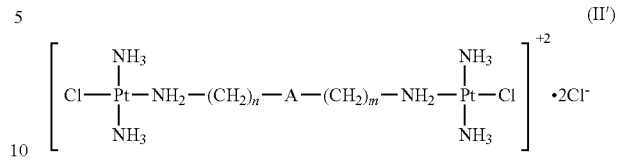

(II')

in which A is as defined in formula I, wherein p is 1 and $Q^{-p}$ is chloride, with a silver carboxylate of formula (III').

The reaction is generally carried out in a solvent such as water, dimethylformamide or mixtures thereof, operating at a temperature ranging from 10 to 60° C. and for a time ranging from 15 hours to 3 weeks, preferably using a molar excess of 6 equivalents of the compound of formula III'; the reaction is generally completed in 2 days.

The compounds of formula (I) in which $Q^{-p}$ is $R^3$—O—$SO_3^-$ can be obtained by reaction of a compound of formula (II) with at least two equivalents of silver nitrate, to give an intermediate which is subsequently reacted with a compound of formula (III), followed by treatment with an alkylsulphate of formula IV.

$R^3$—O—$SO_3$M (IV)

wherein $R^3$ and M are as defined above.

The reaction is generally carried out in a solvent such as water, dimethylformamide, methanol or mixtures thereof, operating at a temperature ranging from 10 to 60° C. and for a time ranging from 15 hours to 3 weeks. Preferably a molar excess (6 equivalents) of the compound of formula (III) and a stoichiometric amount or a slight excess of a compound of formula (IV) are used.

Methods for the preparation of the compounds of formula (II) and (II') are disclosed in U.S. Pat. Nos. 6,022,892 and 6,596,889.

The compounds of formula (III) are commercially available (for example from Sigma-Aldrich, St. Louis (Mo.), USA) or can be prepared with known methods from the corresponding carboxylic acids of formula (V)

RCOOH (V)

wherein R is as defined in formula (I). The compounds of formula (III') can be prepared according to U.S. Pat. No. 5,117,022.

The alkylsulphates of formula (IV) and the carboxylic acids of formula (V) are commercially available (for example from Sigma-Aldrich, St. Louis (Mo.), USA) or can be prepared according to known or methods.

When incubated in the presence of human plasma, the platinum complexes of the present invention showed lower binding activity and better stability than the platinum complexes disclosed in U.S. Pat. No. 6,022,892.

When administered to humans or animals bearing tumors either treatable with or resistant to cisplatin, at doses ranging from 0.1 mg to 1.2 g per $m^2$ of body area, the compounds of the invention induced regression of said tumours.

In general, the compounds of the invention can be used for the treatment of pathological conditions treatable with cisplatin, i.e. for the treatment of tumours and for increasing sensitivity of tumors to radiation therapy [Douple et al., Cisplatin Current Status and Developments, and A. W. Prestayk et al., Academic Press, 125 (1980); Douple et al., Platinum Metals Res., 29; 118 (1985)] and for the treatment of parasitosis such as african trypanosomiasis [Farrell et al., Biochem.

Pharmacol., 33, 961 (1984)]. Therefore, the present invention also comprises a method for the treatment of a tumour in an individual in need thereof, comprising administering to the individual a compound of formula (I) in an amount effective to treat the tumour. As used herein, the term "treatment" may include one or more of the following: the arrest of tumour growth, the killing of tumour cells, the prevention of tumour cells, or the prolongation of survival.

A further embodiment of the invention consists in pharmaceutical compositions containing a therapeutically effective amount of at least one compound of formula (I) in admixture with conventional carriers and excipients.

The effective dose of the compounds of the invention can be determined by the skilled physician according to conventional methods. The relationship between the dosages used for animals of various species and dimensions and those for humans (calculated as mg/m$^2$ of body area) is described by Freirech et al., Quantitative Comparison of Toxicity of Anticancer Agents in Mouse, Rat, Hamster, Dog, Monkey and Man, Cancer Chemother. Rep., 50, N.4, 219-244 (1986). However, the patient will usually receive doses of the complex ranging from 0.1 to 200 mg/kg of body weight, with a dosage regimen which varies according to a number of factors well known to the skilled physician.

The treatment regimen can be suitably adjusted, as well known to experts, according to the tumour to treat and to the conditions of the patient.

The compounds of the invention can be administered through parenteral or oral route.

The pharmaceutical compositions for parenteral use comprise sterile saline solutions, as defined above, or sterile powders for the extemporaneous preparation of solutions, as well as oily preparations for intramuscular (im) or intraperitoneal (ip) administration.

The compounds of the invention are preferably administered as sterile aqueous solutions, optionally containing sodium chloride in suitable concentration (0.1-0.9 mg/ml). The solutions are preferably administered through intravenous (iv) or intra-arterial (ia) route, although in particular cases other administration forms can be used.

Pharmaceutical compositions useful for the oral administration comprise, for example, syrups or analogous liquid forms, as well as solid forms such as tablets, capsules and the like.

The pharmaceutical compositions according to the present invention are prepared according to conventional methods, such as those reported in Remington's Pharmaceutical Sciences Handbook, XVII Ed., Mack Pub., N.Y., U.S.A.

Sometimes it can be advantageous to administer the platinum complexes of the present invention in combination with one or more agents that increase the antitumor activity or alleviate the undesirable side effects which can be associated to the therapy with platinum complexes. For example, the platinum complexes of the present invention can be administered together with reduced glutathione, as described in GB 2,174,905 and in U.S. Pat. No. 4,871,528.

Moreover, it can be advantageous to administer the platinum complexes of the present invention in combination with other antitumour platinum complexes.

Therefore, a further embodiment of the present invention consists in pharmaceutical compositions containing at least one compound of formula (I) in combination with a platinum complex having antitumor activity.

A further embodiment of the present invention consists in the use of the compounds of formula (I) for the preparation of medicaments for the treatment of mammals affected by tumors treatable with or resistant to cisplatin.

The invention is further illustrated in the following examples.

EXAMPLES

Preparation 1: Tetrabutylammonium Caprylate

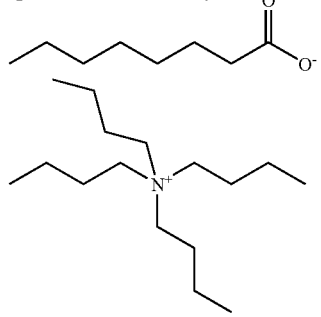

A dispersion of caprylic acid (n-octanoic acid) (1 mL, 6.184 mmoles) in H$_2$O (20 mL) was added with a 0.4 M solution of tetrabutylammonium hydroxide in H$_2$O (15.3 mL, 6.12 mmoles) drop by drop and under stirring. The resulting solution was left under stirring at room temperature for 1 hour and the solvent was then evaporated off under reduced pressure using toluene to remove water. The residue was dried under vacuum at 35° C. to give 2.416 g (>99% yield) of a clear oil.

$^1$H NMR (DMSO-d$_6$): δ 3.18 (8H, t, J=8.34 Hz); 1.73 (2H, t, J=7.39); 1.58 (8H, m); 1.32 (10H, m); 1.22 (8H, m); 0.94 (12H, t, J=7.32); 0.86 (3H, t, J=6.87).

Preparation 2: Tetrabutylammonium Dodecanoate

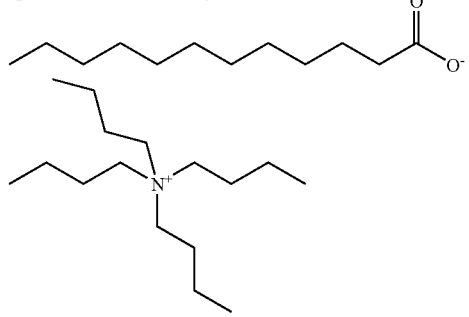

A 0.4 M solution of tetrabutylammonium hydroxide in H$_2$O (1 mL, 0.4 mmoles) was added drop by drop and under stirring to a suspension of dodecanoic acid (0.12 g, 0.6 mmoles) in MilliQ H$_2$O (12 mL). The resulting suspension was left under stirring at room temperature for 1 hour; the solid was removed by filtration and the filtrate was then evaporated to dryness under reduced pressure, using EtOH to remover water. 0.17 g (96% yield) of a yellow oil were obtained.

$^1$H NMR (D$_2$O): δ 3.20 (8H, m); 2.18 (2H, t, J=7.35 Hz); 1.66 (8H, m); 1.37 (8H, m); 1.29 (18H, m); 0.96 (12H, t, J=7.38); 0.87 (3H, m).

With methods similar to preparations 1 and 2 the following compounds were prepared:

tetrabutylammonium caproate
tetrabutylammonium dodecanoate
tetrabutylammonium tridecanoate
tetrabutylammonium myristate
tetrabutylammonium stearate

Example 1

{μ-(1,8,11,18-Tetraazaoctadecane-N$^1$,N$^{18}$)bis[trans-diamino(caproato-O)platinum(II)]}tetranitrate

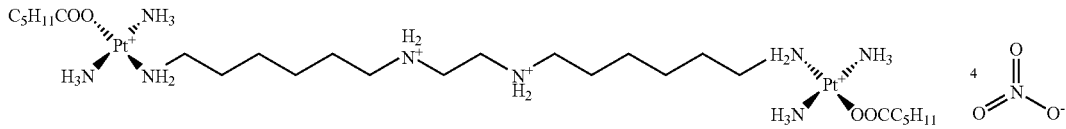

A dispersion of caproic acid (0.16 mL, 1.277 mmoles) in MilliQ H$_2$O (2 mL) was added drop by drop and under stirring to a 0.4 M solution of tetrabutylammonium hydroxide in H$_2$O (2.89 mL, 1.156 mmoles). The resulting solution was left under stirring at room temperature for 1 hour and was then used without further treatment.

The reactions were carried out shielded from light, under nitrogen atmosphere and in MilliQ H$_2$O. AgNO$_3$ (0.0655 g, 0.386 mmoles) was added to a solution of {μ-(1,8,11,18-tetraazaoctadecane-N$^1$,N$^{18}$)bis[trans-diamino(dichloro)platinum(II)]}tetranitrate (0.2 g, 0.193 mmoles) in H$_2$O (12 mL) and the resulting suspension was left under stirring at room temperature for 24 hours. The solid was removed filtering the mixture twice over a double microfiber filter; the filter was washed with 1 mL of H$_2$O which was pooled with the filtrate. The filtrate was added drop by drop and under stirring with the solution of tetrabutylammonium caproate (0.414 g, 1.158 mmoles) in H$_2$O (5 mL); the resulting solution was kept under stirring at room temperature overnight. The solution was evaporated to dryness (35° C.) under reduced pressure and the oily residue was solidified by treatment with absolute EtOH (2 mL). The solid was suspended in Et$_2$O (8 mL) and left under stirring overnight, then collected, suspended in CH$_2$Cl$_2$ (6 mL) and the mixture was kept under stirring overnight. The solid was collected on a buchner filter, washed with CH$_2$Cl$_2$ and dried under vacuum at 40° C. to give 0.055 g (24% yield) of a white powder.

The following compounds were prepared in a similar way
{μ-(1,7,12,18-Tetraazaoctadecane-N$^1$,N$^{18}$)bis[trans-diamino(caproato-O)latinum(II)]}tetranitrate
{μ-(1,5,10,14-Tetraazatetradecane-N$^1$,N$^{14}$)bis)[trans-diamino(caproato-O)platinum(II)]}tetranitrate)
{μ-(1,5,10-Triazadecane-N$^1$,N$^{10}$)bis[trans-diamino(caproato-O) platinum(II)]}tetranitrate

Example 2

{μ-(1,8,11,18-Tetraazaoctadecane-N$^1$,N$^{18}$)bis[trans-diamino(caprylato-O)platinum(II)]}tetranitrate The reactions were carried out shielded from light and in MilliQ H$_2$O. AgNO$_3$ (0.0655 g, 0.386 mmoles) was added to a solution of {μ-(1,8,11,18-tetraazaoctadecane-N$^1$,N$^{18}$)bis[trans-diamino(dichloro)platinum(II)]}tetranitrate (0.2 g, 0.193 mmoles) in H$_2$O (18 mL) and the resulting suspension was left under stirring at room temperature for 24 hours. The solid was removed filtering the mixture twice over a double microfiber filter; the filter was washed with 1 ml H$_2$O which was pooled with the filtrate. The filtrate was added drop by drop and under stirring with a solution of tetrabutylammonium caprylate of preparation 1 (0.462 g, 1.198 mmoles) in H$_2$O (18 mL); the resulting suspension was kept under stirring at room temperature for 23 hours. The sticky material in suspension was removed and the filtrate was concentrated to small volume at 35° C. under reduced pressure. The precipitated solid was collected, dried under vacuum at 35° C. and suspended in CHCl$_3$ (5 mL); the mixture was left under stirring for 1 hour and the solid was collected on a buchner filter and washed with hexane to give 0.025 g (10% yield) of a clear powder.

| Elemental Analysis | Calculated | C | 26.09% | H | 5.89% | N | 14.04% | Pt | 32.59% |
|---|---|---|---|---|---|---|---|---|---|
| | Found | C | 24.88% | H | 5.73% | N | 13.24% | Pt | 31.58% |

MS: 1159.1, [MH+C$_3$F$_7$COOH-4HNO$_3$]$^+$ $^1$H NMR (D$_2$O): δ (3.31 (4H, s); 3.03 (4H, t, J=7.68 Hz); 2.62 (4H, m); 2.26 (4H, t, J=7.53); 1.67 (8H, m); 1.52 (4H, m)T; 1.39 (8H, m); 1.26 (8H, m); 0.86 (6H, t, J=7.03).

| Elemental | Calculated | C | 28.75% | H | 6.27% | N | 13.41% | Pt | 31.13% |
| Analysis | Found | C | 27.72% | H | 6.06% | N | 12.79% | Pt | 29.631% |

MS: 1215.2, $[MH+C_3F_7COOH-4HNO_3]^+$ $^1$H NMR ($D_2O$): δ (3.24 (4H, s); 2.99 (4H, m); 2.62 (4H, t, J=7.64 Hz); 2.26 (4H, t, J=7.53); 1.66 (8H, m); 1.52 (4H, m); 1.39 (8H, m); 1.27 (16H, m); 0.87 (6H, t, J=6.82).

The following compounds were prepared in a similar way

{μ-(1,7,12,18-Tetraazaoctadecane-$N^1,N^{18}$)bis[trans-diamino(caprylato-O)platinum(II)]}tetranitrate {μ-(1,5,10,14-Tetraazatetradecane-$N^1,N^{14}$)bis[trans-diamino(caprylato-O)platinum(II)]}tetranitrate {μ-(1,5,10-Triazadecane-$N^1,N^{10}$)bis[trans-diamino(caprylato-O) platinum(II)]}tetranitrate

Example 3

{μ-(1,8,11,18-Tetraazaoctadecane-$N^1,N^{18}$)bis[trans-diamino(dodecanoato-O)platinum(II)]}tetradodecanoate

MS: 1327.3, $[MH+C_3F_7COOH-4C_{11}H_{23}COOH]^+$ $^1$H NMR ($CDCl_3/CD_3OD$ 75/1): δ 8.47 (2H, s); 2.76 (4H, s); 2.60 (4H, t, J=6.71 Hz); 2.51 (4H, m); 2.16 (8H, t, J=7.60); 2.06 (4H, t, J=7.72); 1.44 (22H, m); 1.17 (102H, m); 0.79 (18H, t, J=6.67).

The following compounds were prepared in a similar way

{μ-(1,7,12,18-Tetraazaoctadecane-$N^1,N^{18}$)bis[trans-diamino(dodecanoato-O)platinum(II)]}tetradodecanoate {μ-(1,5,10,14-Tetraazatetradecane-$N^1,N^{14}$)bis[trans-diamino(dodecanoato-O)platinum(II)]}tetradodecanoate)

{μ-(1,5,10-Triazadecan-$N^1,N^{10}$)bis[trans-diamino(dodecanoato-O) platinum(II)]}tetradodecanoate

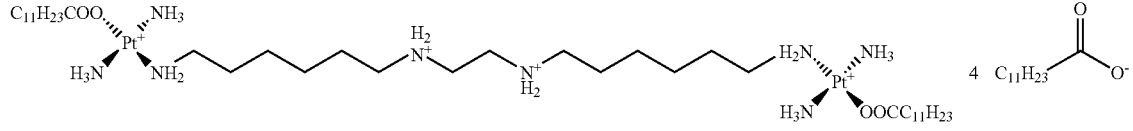

Example 4

{μ-(1,8,11,18-Tetraazaoctadecane-$N^1,N^{18}$)bis[trans-diamino(tridecanoato-O)platinum(II)]}tetratridecanoate

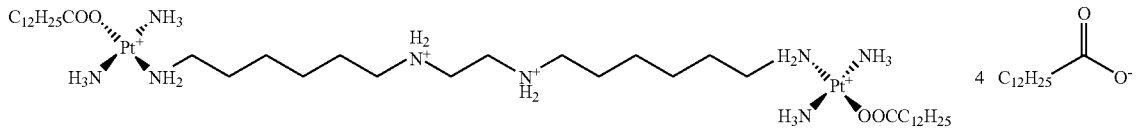

The reactions were carried out shielded from light, under nitrogen atmosphere and in MilliQ $H_2O$. $AgNO_3$ (0.0655 g, 0.386 mmoles) was added to a solution of {μ-(1,8,11,18-tetraazaoctadecane-$N^1,N^{18}$)bis[trans-diamino(dichloro)platinum(II)]}tetranitrate (0.2 g, 0.193 mmoles) in $H_2O$ (10 mL) and the resulting suspension was left under stirring at room temperature for 24 hours. The solid was removed filtering the mixture twice over a microfiber filter; the filter was washed with 4 mL of $H_2O$ which were pooled with the filtrate. The filtrate was added drop by drop and under stirring with a solution of tetrabutylammonium dodecanoate of preparation 2 (0.511 g, 1.158 mmoles) in $H_2O$ (6 mL); the resulting solution was kept under stirring at room temperature overnight. The separated sticky material was collected and suspended in acetone (4 mL); the suspension was left under stirring for 2 hours and the resulting solid was collected on a buchner filter and dried under vacuum at 40° C. to give 0.145 g (39% yield) of a clear powder.

A 0.4M solution of tetrabutylammonium hydroxide in $H_2O$ (2.89 mL, 1.156 mmoles) was added drop by drop and under stirring to a suspension of tridecanoic acid (0.278 g, 1.277 mmoles) in MilliQ $H_2O$ (20 mL). The resulting suspension was left under stirring at room temperature for 1 hour, the solid was removed by filtration and the filtrate was then used without further treatment.

The reactions were carried out shielded from light, under nitrogen atmosphere and in MilliQ $H_2O$. $AgNO_3$ (0.0655 g, 0.386 mmoles) was added to a solution of {μ-(1,8,11,18-tetraazaoctadecane-$N^1,N^{18}$)bis[trans-diamino(dichloro)platinum(II)]}tetranitrate (0.2 g, 0.193 mmoles) in $H_2O$ (23 mL) and the resulting suspension was left under stirring at room temperature for 24 hours. The solid was removed filtering the mixture twice over a double microfiber filter; the filter was washed with 1 ml $H_2O$ which was pooled with the filtrate. The filtrate was added drop by drop and under stirring with the above prepared solution of tetrabutylammonium tridecanoate; the resulting solution was kept under stirring at room temperature overnight. The separated sticky material was collected, washed with $H_2O$, dried under vacuum at 30° C. and suspended in hexane (12 mL); the mixture was left under stirring overnight and the resulting solid was collected on a buchner filter, washed with hexane and dried under vacuum at 30° C. to give 0.098 g (25% yield) of a clear powder.

| Elemental Analysis | Calculated Found | C C | 55.28% 54.42% | H H | 9.99% 9.82% | N N | 5.61% 5.45% | Pt Pt | 19.52% 19.06% |

MS: 1355.3, $[MH+C_3F_7COOH-4C_{12}H_{25}COOH]^+$ $^1H$ NMR ($CD_3OD$): δ 2.89 (4H, s); 2.73 (4H, t, J=7.59 Hz); 2.61 (4H, t, J=7.70); 2.19 (12H, m); 1.60 (20H, m); 1.41 (8H, m); 1.29 (108H, m); 0.90 (18H, t, J=6.83).

The following compounds were prepared in a similar way:

{μ-(1,7,12,18-Tetraazaoctadecane-$N^1,N^{18}$)bis[trans-diamino(tridecanoato-O)platinum(II)]}tetratridecanoate {μ-(1,5,10,14-Tetraazatetradecane-$N^1,N^{14}$)bis[trans-diamino(tridecanoato-O)platinum(II)]}tetratridecanoate)

{μ-(1,5,10-Triazadecane-$N^1,N^{10}$)bis[trans-diamino(tridecanoato-O) platinum(II)]}tetratridecanoate

Example 5

{μ-(1,8,11,18-Tetraazaoctadecane-$N^1,N^{18}$)bis[trans-diamino(myristato-O)platinum(II)]}tetramyristate

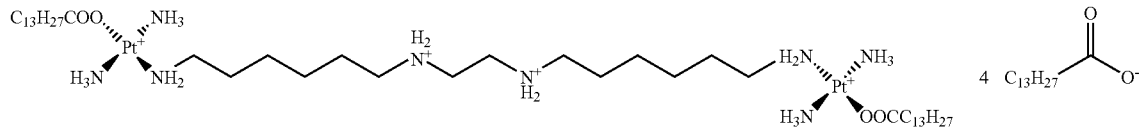

Method A

A 0.4 M solution of tetrabutylammonium hydroxide in $H_2O$ (2.9 mL, 1.16 mmoles) was added drop by drop and under stirring to a suspension of myristic acid (0.53 g, 2.32 mmoles) in MilliQ $H_2O$ (18 mL). The resulting suspension was left under stirring at room temperature for 1 hour; the solid was removed by filtration and the filtrate was then used without further treatment.

The reactions were carried out shielded from light and, in MilliQ $H_2O$. $AgNO_3$ (0.0655 g, 0.386 mmoles) was added to a solution of {μ-(1,8,11,18-tetraazaoctadecane-$N^1,N^{18}$)bis[trans-diamino(dichloro)platinum(II)]}tetranitrate (0.2 g, 0.193 mmoles) in $H_2O$ (18 mL) and the resulting suspension was left under stirring at room temperature for 24 hours. The solid was removed filtering the mixture twice over a double microfiber filter; the filter was washed with 1 mL of $H_2O$ which was pooled with the filtrate. The filtrate was added drop by drop and under stirring to the solution of tetrabutylammonium myristate (1.16 mmoles) in $H_2O$ (18 mL); the resulting suspension was kept under stirring at room temperature for 23 hours and the solid was collected and suspended in $H_2O$ (20 mL). The mixture was left under stirring for 1 hour and the solid was then collected, washed with $H_2O$ and partitioned between $CHCl_3$ (15 mL) and $H_2O$ (15 mL). The diphasic system was left under stirring for 1 h 30'; the organic phase was separated from the aqueous one and evaporated to dryness (35° C.) under reduced pressure. The sticky residue was suspended in hexane (40 mL) and the mixture was kept under stirring for 22 hours. The solid was collected on a buchner filter and washed with hexane to give 0.082 g (20% yield) of a brown powder.

Method B

Step a) Tetrabutylammonium myristate

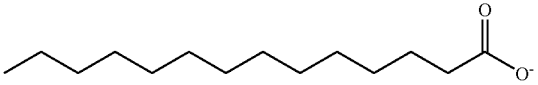

-continued

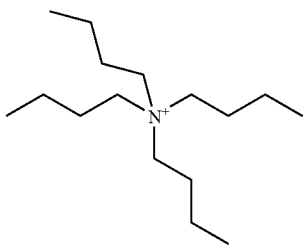

A suspension of myristic acid (1.370 g, 6 mmoles) in MilliQ $H_2O$ (50 mL) was added drop by drop and under stirring with a 0.4M solution of tetrabutylammonium hydroxide in $H_2O$ (10 mL, 4 mmoles). The resulting suspension was stirred at room temperature for 1 hr, the solid was removed by filtration and then evaporated to dryness under reduced pressure using toluene to dry the residue. After drying under vacuum at 35° C., 1.612 g (86% yield) of a brown oil were obtained.

¹H NMR (CDCl₃): δ 3.48 (8H, m); 2.29 (2H, t, J=7.7 Hz); 1.65 (8H, m); 1.45 (8H, m); 1.3 (22H, m); 1.01 (12H, t, J=7.5); 0.88 (3H, t, J=6.6).

Step b) {μ-(1,8,11,18-Tetraazaoctadecane-N¹,N¹⁸)bis[trans-diamino(myristato-O)platinum(II)]}tetramyristate

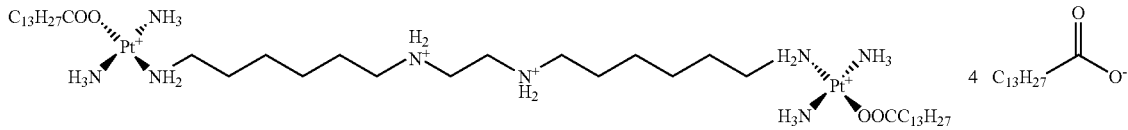

The reactions were carried out shielded from light and in MilliQ H₂O. A solution of {μ-(1,8,11,18-tetraazaoctadecane-N¹,N¹⁸)bis[trans-diamino(dichloro)platinum(II)]}tetranitrate (0.2 g, 0.193 mmoles) in H₂O (18 mL) was added with AgNO₃ (0.0655 g, 0.386 mmoles) and the resulting suspension was added under stirring at room temperature for 24 hrs. The solid was removed filtering the mixture twice on a double microfiber filter; the filter was washed with 1 mL of H₂O which was pooled with the filtrate. The filtrate was added drop by drop and under stirring with the tetrabutylammonium myristate solution (1.16 mmoles) in H₂O (18 mL); the resulting suspension was kept under stirring for 24 hrs and the solid was collected, washed with H₂O and partitioned between CHCl₃ (15 mL) and H₂O (15 mL). The biphasic system was kept under stirring for 1 hr 30'; the organic phase was separated from the aqueous one and evaporated to dryness (35° C.) under reduced pressure. The sticky residue was solidified by treatment with Et₂O followed by evaporation under reduced pressure at 35° C. The solid was collected on a buchner filter and dried under vacuum at 35° C. to give 0.278 g (68% yield) of a clear powder.

| Elemental Analysis | Calculated | C | 56.51% | H | 10.16% | N | 5.38% | Pt | 18.73 |
| --- | --- | --- | --- | --- | --- | --- | --- | --- | --- |
| | Found | C | 58.91% | H | 10.38% | N | 4.25% | Pt | 16.12 |

MS: 1383.4, [MH+C₃F₇COOH-4C₁₃H₂₇COOH]⁺

¹H NMR (CDCl₃/CD₃OD 75/1): δ 2.80 (4H, s); 2.63 (4H, t, J=6.24 Hz); 2.56 (4H, t, J=6.38); 2.15 (8H, t, J=7.54); 2.08 (4H, t, J=7.60); 1.50 (18H, m); 1.20 (130H, m); 0.82 (18H, t, J=6.05).

¹⁹⁵Pt NMR (CDCl₃): δ-2095.81.

The following compounds were prepared in a similar way

{μ-(1,7,12,18-Tetraazaoctadecane-N¹,N¹⁸)bis[trans-diamino(myristato-O)platinum(II)]}tetramyristate {μ-(1,5,10,14-Tetraazatetradecane-N¹,N¹⁴)bis[trans-diamino(myristato-O)platinum(II)]}tetramyristate)

{μ-(1,5,10-Triazadecane-N¹,N¹⁰)bis[trans-diamino(myristato-O) platinum(II)]}tetramyristate Example 6

{μ-(1,8,11,18-Tetraazaoctadecane-N¹,N¹⁸)bis[trans-diamino(stearato-O)platinum(II)]}tetrastearate

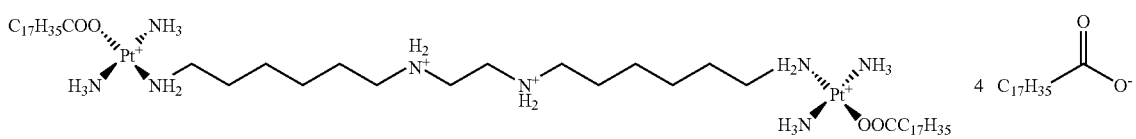

A suspension of stearic acid (0.7 g, 2.461 mmoles) in MilliQ H$_2$O (18 mL) was added with a 0.4 M solution of tetrabutylammonium hydroxide in H$_2$O (2.9 mL, 1.16 mmoles) drop by drop and under stirring. The resulting suspension was left under stirring at room temperature for 1 hour; the solid was removed by filtration and the filtrate was then used without further treatment.

The reactions were carried out shielded from light and in MilliQ H$_2$O. AgNO$_3$ (0.0655 g, 0.386 mmoles) was added to a solution of {μ-(1,8,11,18-tetraazaoctadecane-N$^1$,N$^{18}$)bis[trans-diamino(dichloro)platinum(II)]}tetranitrate (0.2 g, 0.193 mmoles) in H$_2$O (18 mL) and the resulting suspension was left under stirring at room temperature for 24 hours. The solid was removed filtering the mixture twice over a double microfiber filter; the filter was washed with 1 mL of H$_2$O which was pooled with the filtrate. The filtrate was added drop by drop and under stirring with the solution of tetrabutylammonium stearate (1.16 mmoles) in H$_2$O (18 mL) and the resulting suspension was kept under stirring at room temperature for 23 hours. The solid was collected, suspended in H$_2$O (20 mL) and the mixture was left under stirring for 1 hour. The solid was collected on a buchner filter, washed with H$_2$O and dried under vacuum at 35° C. to give 0.349 g (75% yield) of a clear powder.

The reactions were carried out shielded from light and in MilliQ H$_2$O. A solution of {μ-(1,8,11,18-tetraazaoctadecane-N$^1$,N$^{18}$)bis[trans-diamino(dichloro)platinum(II)]}tetranitrate (0.2 g, 0.193 mmoles) in H$_2$O (18 mL) was added with AgNO$_3$ (0.0655 g, 0.386 mmoles) and the resulting suspension was left under stirring at room temperature for 24 hours. The solid was removed filtering the mixture twice over a double microfiber filter; the filter was washed with 1 mL of H$_2$O which was pooled with the filtrate. The filtrate was added drop by drop and under stirring to a sodium decanoate (0.225 g, 1.158 mmoles) solution in H$_2$O (30 mL); the resulting mixture was kept under stirring at room temperature for 6 days. After decantation of the solvent, the sticky material was partitioned between CHCl$_3$ (20 mL) and H$_2$O (20 mL) and the solid undissolved in the diphasic system was removed by filtration. The organic phase was separated from the aqueous one and evaporated to dryness (35° C.) under reduced pressure; the sticky residue solidified by suspension in Et$_2$O, which was then evaporated (35° C.) under reduced pressure. The resulting solid was collected and dried under vacuum at 35° C. to give 0.064 g (19% yield) of a brown powder.

| Elemental | Calculated | C | 60.56% | H | 10.75% | N | 4.63% | Pt | 16.125 |
|---|---|---|---|---|---|---|---|---|---|
| Analysis | Found | C | 60.15% | H | 10.68% | N | 4.20% | Pt | 14.86 |

MS: 1495.4, [MH+C$_3$F$_7$COOH-4C$_{17}$H$_{35}$COOH]$^+$ $^1$H NMR (CDCl$_3$): δ 6.25 (4H, s); 4.46 (12H, s); 2.93 (4H, s); 2.71 (8H, m); 2.22 (8H, t, J=7.65 Hz); 2.15 (4H, t, J=7.79); 1.53 (20H, m); 1.28 (176H, m); 0.90 (18H, t, J=6.81).

$^{195}$Pt NMR (CDCl$_3$): δ-2096.19.

| Elemental | Calculated | C 50.90% | H 9.35% | N 6.42% |
|---|---|---|---|---|
| Analysis | Found | C 48.88% | H 9.66% | N 6.61% |

MS: 1171.4, [MH+CF$_3$COOH-4C$_9$H$_{19}$COOH]$^+$ $^1$H NMR (CDCl$_3$): δ 6.25 (4H, s); 4.45 (12H, s); 2.90 (4H, s); 2.70 (8H, m); 2.15 (12H, m); 1.54 (20H, m); 1.26 (80H, m); 0.87 (18H, m).

The following compounds were prepared in a similar way)
{μ-(1,7,12,18-Tetraazaoctadecane-N$^1$,N$^{18}$)bis[trans-diamino(stearato-O) platinum(II)]}tetrastearate
{μ-(1,5,10,14-Tetraazatetradecane-N$^1$,N$^{14}$)bis[trans-diamino(stearato-O)platinum(II)]}tetrastearate
{μ-(1,5,10-Triazadecane-N$^1$,N$^{10}$)bis[trans-diamino(stearato-O) platinum(II)]}tetrastearate

Example 7

{μ-(1,8,11,18-Tetraazaoctadecane-N$^1$,N$^{18}$)bis[trans-diamino(decanoato-O)platinum(II)]}tetradecanoate The following compounds were prepared in a similar way
{μ-(1,7,12,18-Tetraazaoctadecane-N$^1$,N$^{18}$)bis[trans-diamino(decanoato-O)platinum(II)]}tetradecanoate
{μ-(1,5,10,14-Tetraazatetradecane-N$^1$,N$^{14}$)bis[trans-diamino(decanoato-O)platinum(II)]}tetradecanoate
{μ-(1,5,10-Triazadecane-N$^1$,N$^{10}$)bis[trans-diamino(decanoato-O) platinum(II)]}tetradecanoate

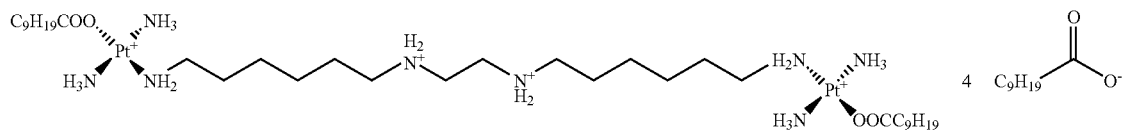

Example 8

{μ-(1,8,11,18-Tetraazaoctadecane-$N^1,N^{18}$)bis[trans-diamino(16-hydroxypalmitato-O)platinum(II)]}tetra(16-hydroxypalmitate)

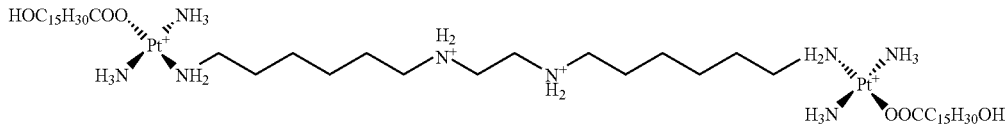

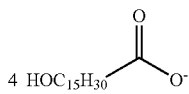

A suspension of 16-hydroxypalmitic acid (0.645 g, 2.3 mmoles) in $H_2O$ MilliQ (18 mL) was added drop by drop and under stirring with a 0.4 M solution of tetrabutylammonium hydroxide in $H_2O$ (2.9 mL, 1.16 mmoles). The resulting suspension was kept under stirring at room temperature for one hour; the solid was removed by filtration and the filtrate was used without further treatment.

The reactions were carried out shielded from light and in MilliQ $H_2O$ water. A solution of {μ-(1,8,11,18-tetraazaoctadecane-$N^1,N^{18}$)bis[trans-diamino(dichloro)platinum(II)]}tetranitrate (0.2 g, 0.193 mmoles) in $H_2O$ (18 mL) was added with $AgNO_3$ (0.072 g, 0.424 mmoles) and the resulting suspension was kept under stirring at room temperature for 24 hrs. The solid was removed filtering the mixture twice on a double microfiber filter; the filter was washed with 1 mL of $H_2O$ that was pooled with the filtrate. The filtrate was added drop by drop and under stirring with a solution of tetrabutylammonium 16-hydroxypalmitate (1.16 mmoles) in $H_2O$ (18 mL); the resulting suspension was kept under stirring at room temperature for 24 hrs and the precipitated solid was collected, washed with $H_2O$ and dried under vacuum at 35° C. An $Et_2O$ (30 mL) suspension of the solid was stirred at room temperature for 1 hr, then the solid was collected on a buchner filter and washed with $Et_2O$ to give 0.428 g (95% yield) of the title product.

MS: 1471.4, $[MH+C_3F_7COOH-4HOC_{15}H_{30}COOH]^+$ $^1H$ NMR ($CD_3OD$): δ 3.54 (12H, t); 2.89 (4H, s); 2.73 (4H, m); 2.61 (4H, m); 2.20 (12H, m); 1.60 (30H, m); 1.40 (6H, m); 1.35 (136H, m).

The following compounds were prepared in a similar way:

{μ-(1,7,12,18-Tetraazaoctadecane-$N^1,N^{18}$)bis[trans-diamino(16-hydroxypalmitato-O)platinum(II)]}tetra(16-hydroxypalmitate)

{μ-(1,5,10,14-Tetraazatetradecane-$N^1,N^{14}$)bis[trans-diamino(16-hydroxypalmitato-O)platinum(II)]}tetra(16-hydroxypalmitate)

{μ-(1,5,10-Triazadecane-$N^1,N^{10}$)bis[trans-diamino(16-hydroxypalmitato-O)platinum(II)]}tetra(16-hydroxypalmitate)

Example 9

{μ-(1,7,12,18-Tetraazaoctadecane-$N^1,N^{18}$)bis[trans-diamino(butyrato-O)platinum(II)]}tetrabutyrate

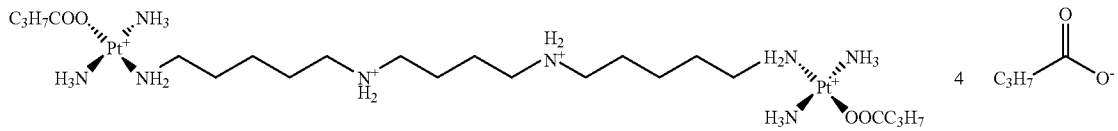

The reactions were carried out shielded from light and in MilliQ $H_2O$. A solution of {μ-(1,7,12,18-tetraazaoctadecane-$N^1,N^{18}$)bis[trans-diamino(dichloro)platinum(II)]}tetranitrate (0.2 g, 0.193 mmoles) in $H_2O$ (18 mL) was added with $AgNO_3$ (0.0655 g, 0.386 mmoles) and the resulting suspension was kept under stirring at room temperature for 48 hours. The solid was washed filtering the mixture twice on a double microfiber filter; the filter was washed with 1 mL of $H_2O$ that was pooled with the filtrate. The filtrate was added with sodium butyrate (0.127 g, 1.154 mmoles) and the solution was kept under stirring at room temperature for 24 hrs. The

| Elemental | Calculated | C | 56.29% | H | 10.05% | N | 4.77% | Pt | 16.62% |
| Analysis | Found | C | 55.53% | H | 9.97% | N | 4.33% | Pt | 15.14% | solvent was evaporated at 35° C. under reduced pressure and the solid residue was dried under vacuum at 35° C. The solid was then suspended in i-PrOH (20 mL) and the suspension was maintained under stirring at room temperature for 1 hr. The insoluble material was removed by filtration and the filtrate was evaporated under vacuum (35° C.) at room temperature. The solid residue was collected on a buchner filter, washed with $Et_2O$ and dried under vacuum at 35° C. to give 0.149 g (62% yield) of the title product as a white solid.

| Elemental | Calculated | C | 36.77% | H | 7.31% | N | 9.03% | Pt | 31.43% |
| Analysis | Found | C | 33.59% | H | 6.69% | N | 9.18% | Pt | 31.78% |

MS: 1103.0, $[MH+C_3F_7COOH-4C_3H_7COOH]^+$ $^1H$ NMR ($D_2O$): δ 3.04 (8H, m); 2.63 (4H, t, J=7.5 Hz); 2.24 (4H, t, J=7.3); 2.16 (8H, t, J=7.3); 1.72 (12H, m); 1.56 (12H, m); 1.43 (4H, m); 0.88 (18H, m).

The following compounds were prepared in a similar way:

{µ-(1,7,12,18-Tetraazaoctadecane-$N^1,N^{18}$)bis[trans-diamino(butyrato-O)platinum(II)]}tetrabutyrate {µ-(1,5,10,14-Tetraazatetradecane-$N^1,N^{14}$)bis[trans-diamino(butyrato-O)platinum(II)]}tetrabutyrate {µ-(1,5,10-Triazadecane-$N^1,N^{10}$)bis[trans-diamino(butyrato-O)platinum(II)]}tetrabutyrate Example 10

{µ-(1,8,11,18-Tetraazaoctadecane-$N^1,N^{18}$)bis[trans-diamino(caprylato-O)platinum(II)]}tetracaprylate

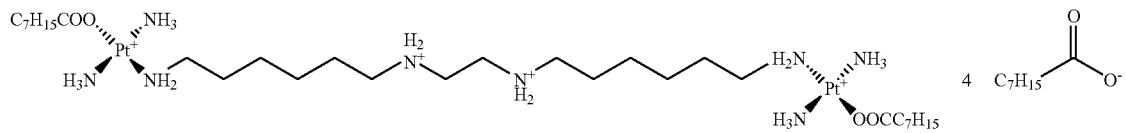

The reactions were carried out shielded from the light and in MilliQ $H_2O$. A solution of {µ-(1,8,11,18-tetraazaoctadecane-$N^1,N^{18}$)bis[trans-diamino(dichloro)platinum(II)]}tetranitrate (0.2 g, 0.193 mmoles) in $H_2O$ (18 mL) was added with $AgNO_3$ (0.0655 g, 0.386 mmoles) and the resulting suspension was left under stirring at room temperature for 48 hours. The solid was removed filtering the mixture twice on a double microfiber filter; the filter was washed with 1 mL of $H_2O$ that was added to the filtrate. The filtrate was added drop by drop and under stirring to a solution of sodium caprylate (0.192 g, 1.155 mmoles) in MeOH (19 mL); the resulting solution was maintained under stirring at room temperature for 24 hrs. The filtrate was concentrated to half volume (35° C.) under reduced pressure and the separated oil was dissolved by addition of $CHCl_3$ (18 mL). After stirring for 10 minutes at room temperature, the organic phase was separated from the aqueous one and evaporated to dryness (35° C.) under reduce pressure. The oily residue was solidified by addition of $Et_2O$ followed by evaporation under reduced pressure (35° C.). The solid was collected on a buchner filter and dried under vacuum at 35° C. to give 0.217 g (yield 71%) of the title product as a white solid.

| Elemental | Calculated | C | 47.19% | H | 8.82% | N | 7.10% | Pt | 24.72% |
| Analysis | Found | C | 46.89% | H | 8.70% | N | 7.03% | Pt | 24.25% |

MS: 1215.1, [MH+C$_3$F$_7$COOH-4C$_7$H$_{15}$COOH]$^+$ $^1$H NMR (CDCl$_3$): δ 6.20 (4H, s); 4.40 (12H, s); 2.93 (4H, s); 2.73 (8H, m); 2.21 (8H, t, J=7.5 Hz); 2.15 (4H, t, J=7.5); 1.54 (20H, m); 1.30 (56H, m); 0.90 (18H, m).

The following compounds were prepared in a similar way:

{μ-(1,7,12,18-Tetraazaoctadecane-N$^1$,N$^{18}$)bis[trans-diamino(caprylato-O)platinum(II)]}tetracaprylate {μ-(1,5,10,14-Tetraazatetradecane-N$^1$,N$^{14}$)bis[trans-diamino(caprylato-O)platinum(II)]}tetracaprylate {μ-(1,5,10-Triazadecane-N$^1$,N$^{10}$)bis[trans-diamino(caprylato-O)platinum(II)]}tetracaprylate Example 11

{μ-(1,8,11,18-Tetraazaoctadecane-N$^1$,N$^{18}$)bis[trans-diamino(caproato-O)platinum(II)]}tetracaprate

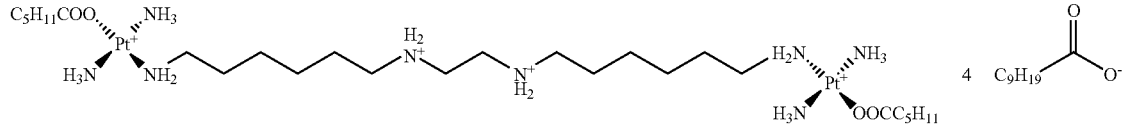

The reactions were carried out shielded from light and in MilliQ H$_2$O. A solution of {μ-(1,8,11,18-tetraazaoctadecane-N$^1$,N$^{18}$)bis[trans-diamino(caproato-O)platinum(II)]}tetranitrate of Example 1 (0.441 g, 0.368 mmoli) in H$_2$O (25 mL) was added with a solution of sodium caprate (0.286 g, 1.472 mmoles) in H$_2$O (5 mL) drop by drop and under stirring; the resulting mixture was kept under stirring at room temperature for 15 min. The gelly material which separated from the mixture was dissolved by addition of CHCl$_3$ (25 mL). After stirring for 15 min. at room temperature, the organic phase was separated from the aqueous one and evaporated to dryness at 35° C. under reduced pressure. The oily residue was solidified by treatment with Et$_2$O and evaporation at 35° C. under reduced pressure. The solid was collected on a buchner filter and dried under vacuum at 35° C. to give 0.387 g (64% yield) of the title product.

| Elemental | Calculated | C | 48.51% | H | 9.01% | N | 6.86% | Pt | 23.88% |
| Analysis | Found | C | 48.09% | H | 8.99% | N | 6.62% | Pt | 23.31% |

MS: 1159.0, [MH+C$_3$F$_7$COOH-4C$_9$H$_{19}$COOH]$^+$ $^1$H NMR (CD$_3$OD): δ 2.88 (4H, s); 2.73 (4H, t); 2.61 (4H, m); 2.19 (12H, m); 1.6 (18H, m); 1.41 (8H, m); 1.3 (58H, m); 0.9 (18H, m).

The following compounds were prepared in a similar way:

{μ-(1,7,12,18-Tetraazaoctadecane-N$^1$,N$^{18}$)bis[trans-diamino(caproato-O)platinum(II)]}tetracaprate {μ-(1,5,10,14-Tetraazatetradecane-N$^1$,N$^{14}$)bis[trans-diamino(caproato-O)platinum(II)]}tetracaprate)

{μ-(1,5,10-Triazadecane-N$^1$,N$^{10}$)bis[trans-diamino(caproato-O)platinum(II)]}tetracaprate

Example 12

{μ-(1,8,11,18-Tetraazaoctadecane-N¹,N¹⁸)bis[trans-diamino(piyalato-O)platinum(II)]}tetra(dodecylsulphate)

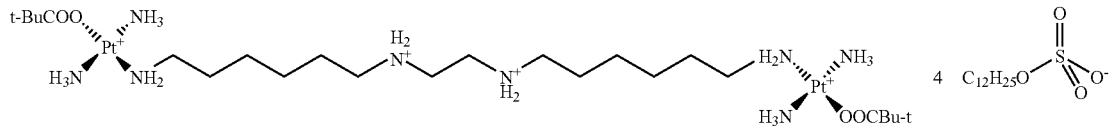

The reactions were carried out shielded from light and in H₂O MilliQ. A solution of {μ-(1,8,11,18-tetraazaoctadecane-N¹,N¹⁸)bis[trans-diamino(dichloro)platinum(II)]}tetranitrate (0.2 g, 0.193 mmoles) in H₂O (18 mL) was added with AgNO₃ (0.072 g, 0.424 mmoles) and the resulting suspension was left under stirring at room temperature for 24 hrs. The solid was removed filtering the mixture twice on a double microfiber filter and the filter was washed with 1 mL of H₂O that was pooled with the filtrate. The filtrate was added drop by drop and under stirring with a solution of sodium pivalate hydrate (0.144 g, 1.16 mmoles) in MeOH (19 mL); the resulting solution was kept under stirring at room temperature for 24 hours, then concentrated to half volume (35° C.) under reduced pressure, and added with a sodium dodecylsulphate solution (0.222 g, 0.77 mmoles) in H₂O (15 mL) drop by drop and under stirring. After stirring for 15 minutes at room temperature, the precipitated solid was collected on a buchner filter and dried under vacuum at 35° C. to give 0.262 g (68% yield) of the title product.

| Elemental Analysis | | | | | | | | | | |
|---|---|---|---|---|---|---|---|---|---|---|
| Calculated | C | 43.62% | H | 8.44% | N | 5.65% | Pt | 19.68% | S | 6.47% |
| Found | C | 43.48% | H | 8.27% | N | 5.77% | Pt | 19.69% | S | 6.03% |

MS: 1131.1, [MH+C₃F₇COOH-4C₁₂H₂₅OSO₃H]⁺
¹H NMR (CD₃OD): δ 4.17 (12H, bs); 4.00 (8H, t, J=6.77 Hz); 3.19 (4H, s); 2.97 (4H, m); 2.65 (4H, m); 1.67 (16H, m); 1.52-1.24 (80H, m); 1.10 (18H, s); 0.90 (12H, t, J=7.14).

The following compounds were prepared in a similar way:
{μ-(1,7,12,18-Tetraazaoctadecane-N¹,N¹⁸)bis[trans-diamino(pivalato-O)platinum(II)]}tetra(dodecylsulphate)
{μ-(1,5,10,14-Tetraazatetradecane-N¹,N¹⁴)bis[trans-diamino(pivalato-O)platinum(II)]}tetra(dodecylsulphate)
{μ-(1,5,10-Triazadecane-N¹,N¹⁰)bis[trans-diamino(pivalato-O)platinum(II)]}tetra(dodecylsulphate)

Example 13

{μ-(1,8,11,18-Tetraazaoctadecane-N¹,N¹⁸)bis[trans-diamino(capronato-O)platinum(II)]}tetra(dodecylsulphate)

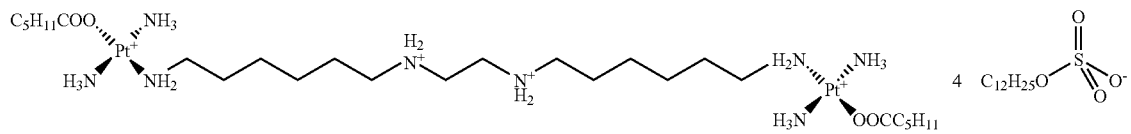

The reactions were carried out shielded from light and in MilliQ $H_2O$. A solution of {μ-(1,8,11,18-tetraazaoctadecane-$N^1,N^{18}$)bis[trans-diamino(dichloro)platinum(II)]}tetranitrate (0.2 g, 0.193 mmoles) in $H_2O$ (18 mL) was added with $AgNO_3$ (0.072 g, 0.424 mmoles) and the resulting suspension was kept under stirring for 24 hrs. The solid was removed filtering the mixture twice on a double microfibre filter and the filter was washed with 1 mL of $H_2O$ which was pooled with the filtrate. The filtrate was added drop by drop and under stirring with a sodium capronate solution (0.16 g, 1.158 mmoles) in MeOH (19 mL); the resulting solution was maintained under stirring at room temperature for 24 hrs, then concentrated to half volume (35° C.) under reduced pressure and added drop by drop and under stirring with a sodium dodecylsulphate solution (0.222 g, 0.77 mmoles) in $H_2O$ (15 mL). After stirring for 15 min at room temperature, the precipitated solid was collected on a buchner filter, washed with few millilitres of water and dried under vacuum at 35° C. to give 0.301 g (78% yield) of the title product.

| Elemental | Calculated | C | 44.21% | H | 8.52% | N | 5.57% | Pt | 19.40% | S | 6.38% |
| Analysis | Found | C | 43.53% | H | 8.42% | N | 5.45% | Pt | 19.02% | S | 6.80% |

$^1$H NMR ($CD_3OD$): δ 4.17 (12H, bs); 4.00 (8H, t, J=6.58 Hz); 3.20 (4H, s); 2.98 (4H, t, J=7.5); 2.65 (4H, m); 2.18 (4H, t, J=8.24); 1.76-1.21 (108H, m); 0.90 (18H, m).

The following compounds were prepared in a similar way:

{μ-(1,7,12,18-Tetraazaoctadecane-$N^1,N^{18}$)bis[trans-diamino(capronato-O)platinum(II)]}tetra(dodecylsulphate)

{μ-(1,5,10,14-Tetraazatetradecane-$N^1,N^{14}$)bis[trans-diamino(capronato-O)platinum(II)]}tetra(dodecylsulphate)

{μ-(1,5,10-Triazadecane-$N^1,N^{10}$)bis[trans-diamino(capronato-O)platinum(II)]}tetra(dodecylsulphate)

Example 14

{μ-(1,8,11,18-Tetraazaoctadecane-$N^1,N^{18}$)bis[trans-diamino(butyrato-O)platinum(II)]}tetra(dodecylsulphate)

The reactions were carried out shielded from light and in MilliQ $H_2O$. A solution of {μ-(1,8,11,18-tetraazaoctadecane-$N^1,N^{18}$)bis[trans-diamino(dichloro)platinum(II)]}tetranitrate (0.2 g, 0.193 mmoles) in $H_2O$ (18 mL) was added with $AgNO_3$ (0.072 g, 0.424 mmoles) and the resulting suspension was left under stirring at room temperature for 24 hours. The solid was removed filtering the mixture twice on a double microfiber filter; the filter was washed with 1 mL of $H_2O$ which was added to the filtrate. The filtrate was added with sodium butyrate (0.127 g, 1.154 mmoles) and the resulting solution was kept under stirring at room temperature for 24 hrs, then added drop by drop and under stirring with a sodium dodecylsulphate solution (0.222 g, 0.77 mmoles) in $H_2O$ (10 mL). After stirring for 15 minutes at room temperature, the precipitated solid was collected on a buchner filter, washed with few millilitres of $H_2O$ and dried under vacuum at 35° C. to give 0.28 g (74% yield) of the title product.

| Elemental | Calculated | C | 43.02% | H | 8.35% | N | 5.73% | Pt | 19.96% | S | 6.56% |
| Analysis | Found | C | 42.72% | H | 8.46% | N | 5.62% | Pt | 19.66% | S | 6.69% |

MS: 1103.0, $[MH+C_3F_7COOH-4C_{12}H_{25}OSO_3H]^+$ $^1$H NMR ($CD_3OD$): δ 4.17 (12H, bs); 4.01 (8H, t, J=6.58 Hz); 3.37 (4H, s); 3.10 (4H, t, J=6.95); 2.66 (4H, m); 2.17 (4H, t, J=7.68); 1.80-1.22 (100H, m); 0.90 (18H, m).

The following compounds were prepared in a similar way:

{μ-(1,7,12,18-tetraazaoctadecane-$N^1,N^{18}$)bis[trans-diamino(butyrato-O)platinum(II)]}tetra(dodecylsulphate)

{μ-(1,5,10,14-Tetraazatetradecane-$N^1,N^{14}$)bis[trans-diamino(butyrato-O)platinum(II)]}tetra(dodecylsulphate)

{μ-(1,5,10-Triazadecane-$N^1,N^{10}$)bis[trans-diamino(butyrato-O)platinum(II)]}tetra(dodecylsulphate)

Example 15

Pharmacological Evaluation of the Compounds of the Invention

Representative compounds of the invention were tested for their cytotoxic effect in vitro on various tumours cell lines, among which murine leukemia L1210, human ovary carcinoma A2780 or the respective cisplatin resistant sub-lines L1210/CDDP and A2780/CDDP. The representative compounds of the invention exhibited cytotoxic effects and they were able to overcome the resistance mechanisms that limit the use of cisplatin.

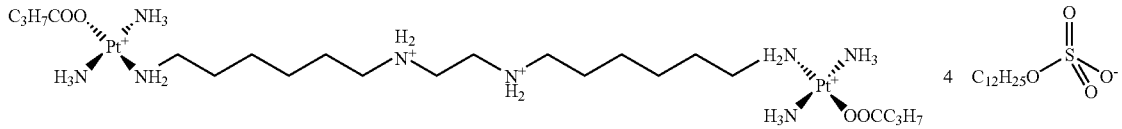

Moreover, representative compounds of the invention were tested in in vivo tests in which human tumor cell lines, for example A2780 (human ovary), A2780/CDDP (human ovary resistant to cisplatin) or LoVo (human colon), were inoculated subcutaneously in immunosuppressed nude mice. The compounds were administered intravenously every four days or every seven days after inoculation of the tumour, for three cycles of treatment. In these experimental models the compounds of the invention evidenced a high antitumour effect at tolerated doses.

The invention claimed is:

1. A compound of formula (I):

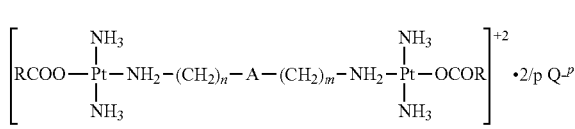

in which:
R is selected from the group consisting of $(C_2-C_{25})$alkyl and $(C_2-C_{25})$alkenyl,
wherein R taken together with the carboxylate group to which it is bound is the residue of a saturated, mono-unsaturated or poly-unsaturated fatty acid;
n and m are each independently an integer of two to eight;
p is one or two;
A is selected from the group consisting of —B—, —B—$(CH_2)_r$—B—, and —B—$(CH_2)_r$—B—$(CH_2)_z$—B—, wherein r and z are an integer from 2 to 8, and B is a —$NR^1$— or —$N(R^2)_2{}^+1/pQ^{-p}$ group, in which $R^1$ is selected from hydrogen, $(C_1-C_4)$alkyl, $(C_1-C_4)$acyl, tert-butoxycarbonyl, and $R^2$ is selected from hydrogen and $(C_1-C_4)$alkyl; and
$Q^{-p}$ is an anion selected from chloride, bromide, iodide, nitrate, sulphate, hydrogen sulphate, perchlorate, $R^3COO^-$ wherein $R^3$ has the same meanings as R, independently from one another, and $R^4$—O—$SO_3^-$ wherein $R^4$ is $(C_2-C_{14})$alkyl
with the proviso that, when $Q^{-p}$ is selected from chloride, bromide, iodide, nitrate, sulphate, hydrogen sulphate, perchlorate, R is not $(C_2-C_4)$alkyl.

2. The compound according to claim 1 in which R taken together the carboxylate group to which it is bound is the residue of a saturated fatty acid having from 10 to 24 carbon atoms.

3. The compound according to claim 1 in which the saturated fatty acid is selected from butyric acid, valeric acid (pentanoic acid), caproic acid (hexanoic acid), enanthic acid (heptanoic acid, caprylic acid (octanoic acid), caproic acid (decanoic acid), neodecanoic acid, lauric acid (dodecanoic acid), myristic acid (tetradecanoic acid), palmitic acid (hexadecanoic acid), stearic acid (octadecanoic acid), arachidic acid (eicosanoic acid), behenic acid (docosanoic acid), lignoceric acid (tetracosanoic acid), 15-hydroxypentadecanoic acid, 16-hydroxypalmitic acid (16-hydroxyhexadecanoic acid; juniperic acid), 6-hydroxypalmitic acid, (R)-7-hydroxyhexadecanoic acid, 17-hydroxyheptadecanoic acid, (S)-9-hydroxyoctadecanoic acid, (S)-13-hydroxyoctadecanoic acid, 12-hydroxystearic acid (12-hydroxyoctadecanoic acid), erythro-6,7-dihydroxyoctadecanoic acid, threo-9,10-dihydroxystearic acid, erythro-9,10-dihydroxystearic acid, erythro-12,13-dihydroxyoctadecanoic acid, and erythro-15,16-dihydroxyoctadecanoic acid.

4. The compound according to claim 1 in which R taken together with the carboxylate group to which it is bound is the residue of an unsaturated fatty acid having from 16 to 22 carbon atoms.

5. The compound according to claim 1 in which the unsaturated acid is selected from oleic acid (cis-9-octadecenoic acid), ricinoleic acid ((R)-12-hydroxy-cis-9-octadecenoic acid; 12-hydroxyoleic acid), erucic acid (cis-13-docosenoic acid); linoleic acid (cis,cis-6,9-octadecadienoic acid), linoledailic acid (trans,trans-9,12-octadecadienoic acid), linolenic acid (cis,cis,cis-9,12,15-octadecatrienoic acid), γ-linolenic acid (cis,cis,cis-6,9,12-octadecatrienoic acid), linolenelaidic acid (trans,trans,trans-9,12,15-octadecatrienoic acid), arachidonic acid (cis,cis,cis,cis-5,8,11,14-eicosatetraenoic acid), cis,cis,cis,cis,cis-5,8,11,14,17-eicosapentaenoic acid (EPA), cis,cis,cis,cis,cis-4,7,10,13,16,19-docosaesenoic acid (DHA), and 4(E),7(Z),10(Z),13(Z),16(Z),19(Z)-docosaesaenoic acid.

6. The compound according claim 1 in which the $H_2N$—$(CH_2)_n$-A-$(CH_2)_m$—$NH_2$ moiety is one of the following:

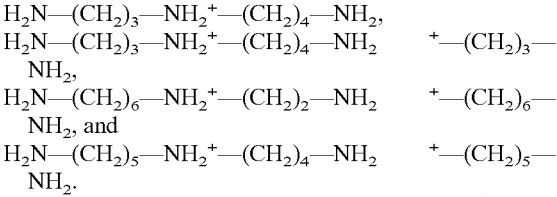

7. The compound according to claim 1 in which $R^4OSO_3^-$ is selected from n-hexyl sulphate, 2-ethylhexylsulphate, n-octylsulphate, n-decylsulphate and n-dodecylsulphate.

8. The compound according to claim 7 wherein $R^4$—O—$SO_3^-$ is n-dodecylsulphate.

9. The compound according to claim 1 in admixture with suitable carriers or excipients.

10. A method for treatment of a tumour in an individual in need thereof, comprising administering to the individual a compound according to claim 1 in an amount effective to treat the tumour.

11. The compound according to claim 1 in which $Q^{-p\ is\ a\ R4}OSO_3^-$ group selected from n-hexyl sulphate, 2-ethylhexylsulphate, n-octylsulphate, n-decylsulphate and n-dodecylsulphate; and in which the $H_2N$—$(CH_2)_n$-A-$(CH_2)_m$—$NH_2$ moiety is one of the following:

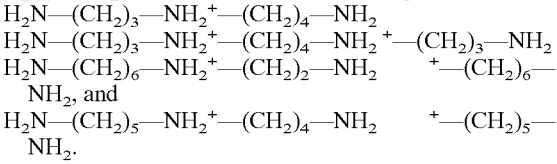

12. The compound according to claim 1 in which:
R is $(C_3-C_7)$alkyl;
n and m are each independently five or six;
A is —B—$(CH_2)_r$—B—, wherein r is an integer from 2 to 4, and B is a —$NR^1$— or —$N(R^2)_2{}^+1/pQ^{-p}$ group, in which $R^1$ and $R^2$ are hydrogen; and
with the proviso that, when Q-p is selected from chloride, bromide, iodide, nitrate, sulphate, hydrogen sulphate, or perchorate, R is not $(C_3-C_4)$alkyl.

13. The compound according to claim 1 in which the $H_2N$—$(CH_2)_n$-A-$(CH_2)_m$—$NH_2$ moiety is one of the following:

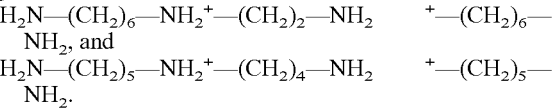

14. The compound according to claim 1 selected from:
{μ-(1,8,11,18-tetraazaoctadecane-$N^1,N^{18}$)bis[trans-diamino(caproato-O)platinum(II)]}tetranitrate,
{μ-(1,7,12,18-tetraazaoctadecane-$N^1,N^{18}$)bis[trans-diamino(caproato- O)platinum(II)]}tetranitrate,
{μ-(1,5,10,14-tetraazatetradecane-$N^1,N^{14}$)bis[trans-diamino(caproato-O)platinum(II)]}tetranitrate,
{μ-(1,5,10-triazadecane-$N^1,N^{10}$)bis[trans-diamino(caproato-O)platinum(II)]}tetranitrate,
{μ-(1,8,11,18-tetraazaoctadecane-$N^1,N^{18}$)bis[trans-diamino(caprylato- O)platinum(II)]}tetranitrate, {μ-(1,7,12,18-tetraazaoctadecane-$N^1,N^{18}$)bis[trans-diamino(caprylato-O)platinum(II)]}tetranitrate, {μ-(1,5,10,14-tetraazatetradecane-$N^1,N^{14}$)bis[trans-diamino(caprylato-O)platinum(II)]}tetranitrate, {μ-(1,5,10-triazadecane-$N^1,N^{10}$)bis[trans-diamino(caprylato-O)platinum(II)]}tetranitrate, {μ-(1,7,12,18-tetraazaoctadecane-$N^1,N^{18}$)bis[trans-diamino(butyrato-O)platinum(II)]}tetrabutyrate, {μ-(1,5,10,14-tetraazatetradecane-$N^1,N^{14}$)bis[trans-diamino(butyrato-O)platinum(II)]}tetrabutyrate, and {μ-(1,5,10-triazadecane-$N^1,N^{10}$)bis[trans-diamino(butyrato-O)platinum(II)]}tetrabutyrate.

15. A compound according to claim 14 which is {μ-(1,8,11,18-tetraazaoctadecane-$N^1,N^{18}$)bis[trans-diamino(caproato-O)platinum(II)]}tetranitrate.

16. A compound according to claim 14 which is {μ-(1,8,11,18-tetraazaoctadecane-$N^1,N^{18}$)bis[trans-diamino(caprylato-O)platinum(II)]}tetranitrate.

17. A compound according to claim 14 which is {μ-(1,7,12,18-tetraazaoctadecane-$N^1,N^{18}$)bis[trans-diamino(butyrato-O)platinum(II)]}tetrabutyrate.

* * * * *